(12) United States Patent
Moschella et al.

(10) Patent No.: US 11,331,045 B1
(45) Date of Patent: May 17, 2022

(54) SYSTEMS AND METHODS FOR MITIGATING NEUROMUSCULAR SIGNAL ARTIFACTS

(71) Applicant: Facebook Technologies, LLC, Menlo Park, CA (US)

(72) Inventors: Anthony D. Moschella, New York, NY (US); Daniel Wetmore, New York, NY (US); Patrick Kaifosh, New York, NY (US); Adam Al-natsheh, New York, NY (US); Tudor Giurgica-Tiron, New York, NY (US); Qiushi Mao, New York, NY (US)

(73) Assignee: Facebook Technologies, LLC, Menlo Park, CA (US)

( * ) Notice: Subject to any disclaimer, the term of this patent is extended or adjusted under 35 U.S.C. 154(b) by 0 days.

(21) Appl. No.: 16/862,050

(22) Filed: Apr. 29, 2020

Related U.S. Application Data

(63) Continuation-in-part of application No. 16/258,279, filed on Jan. 25, 2019, now abandoned.
(Continued)

(51) Int. Cl.
*A61B 5/00* (2006.01)
*A61B 5/24* (2021.01)
(Continued)

(52) U.S. Cl.
CPC .............. *A61B 5/7207* (2013.01); *A61B 5/24* (2021.01); *A61B 5/316* (2021.01); *A61B 5/389* (2021.01);
(Continued)

(58) Field of Classification Search
CPC ......... A61B 5/7207; A61B 5/389; A61B 5/24; A61B 5/316; A61B 5/681; A61B 5/7264; A61B 5/742
See application file for complete search history.

(56) References Cited

U.S. PATENT DOCUMENTS

| 4,055,168 A | 10/1977 | Miller et al. |
| 4,896,120 A | 1/1990 | Kamil |

(Continued)

FOREIGN PATENT DOCUMENTS

| CA | 2 902 045 A1 | 8/2014 |
| CA | 2 921 954 A1 | 2/2015 |

(Continued)

OTHER PUBLICATIONS

International Search Report and Written Opinion for International Application No. PCT/US2017/043686 dated Oct. 6, 2017.
(Continued)

*Primary Examiner* — Raymond L Nimox
(74) *Attorney, Agent, or Firm* — FisherBroyles, LLP

(57) ABSTRACT

The disclosed systems and methods are generally directed to interpreting neuromuscular signals. The system includes (A) a plurality of neuromuscular sensors that detect a plurality of neuromuscular signals from a user and (B) at least one multiplexer in communication with the plurality of neuromuscular sensors and that is capable of dynamically adjusting neuromuscular sensor processing based on neuromuscular signal characteristics. A computer processor is programmed to (i) receive a set of neuromuscular signals from the plurality of neuromuscular sensors, (ii) determine, via a real-time system, at least one signal characteristic included in a neuromuscular signal, where the neuromuscular signal is associated with a first neuromuscular sensor included in the plurality of neuromuscular sensors; and (iii) dynamically reconfigure the processing of neuromuscular signals from the plurality of neuromuscular sensors based on an output from the multiplexer. Various other methods, systems, and computer-readable media are also disclosed.

20 Claims, 13 Drawing Sheets

Related U.S. Application Data

(60) Provisional application No. 62/841,061, filed on Apr. 30, 2019, provisional application No. 62/621,829, filed on Jan. 25, 2018.

(51) Int. Cl.
  *A61B 5/316* (2021.01)
  *A61B 5/389* (2021.01)

(52) U.S. Cl.
  CPC ............ *A61B 5/681* (2013.01); *A61B 5/7264* (2013.01); *A61B 5/742* (2013.01)

(56) References Cited

U.S. PATENT DOCUMENTS

| | | | |
|---|---|---|---|
| 5,625,577 A | 4/1997 | Kunii et al. | |
| 6,005,548 A | 12/1999 | Latypov et al. | |
| 6,009,210 A | 12/1999 | Kand | |
| 6,244,873 B1 | 6/2001 | Hill et al. | |
| 6,411,843 B1 | 6/2002 | Zarychta | |
| 6,658,287 B1 | 12/2003 | Litt et al. | |
| 6,720,984 B1 | 4/2004 | Jorgensen et al. | |
| 6,774,885 B1 | 8/2004 | Even-Zohar | |
| 6,901,286 B1 | 5/2005 | Sinderby et al. | |
| 6,942,621 B2 | 9/2005 | Avinash et al. | |
| 7,089,148 B1 | 8/2006 | Bachmann et al. | |
| 7,351,975 B2 | 4/2008 | Brady et al. | |
| 7,574,253 B2 | 8/2009 | Edney et al. | |
| 7,580,742 B2 | 8/2009 | Tan et al. | |
| 7,787,946 B2 | 8/2010 | Stahmann et al. | |
| 7,805,386 B2 | 9/2010 | Greer | |
| 7,901,368 B2 | 3/2011 | Flaherty et al. | |
| 8,170,656 B2 | 5/2012 | Tan et al. | |
| 8,190,249 B1 | 5/2012 | Gharieb et al. | |
| 8,311,623 B2 | 11/2012 | Sanger | |
| 8,351,651 B2 | 1/2013 | Lee | |
| 8,421,634 B2 | 4/2013 | Tan et al. | |
| 8,435,191 B2 | 5/2013 | Barboutis et al. | |
| 8,437,844 B2 | 5/2013 | Syed Momen et al. | |
| 8,447,704 B2 | 5/2013 | Tan et al. | |
| 8,484,022 B1 | 7/2013 | Vanhoucke | |
| 8,718,980 B2 | 5/2014 | Garudadr et al. | |
| 8,744,543 B2 | 6/2014 | Li et al. | |
| 8,754,862 B2 | 6/2014 | Zaliva | |
| D717,685 S | 11/2014 | Bailey et al. | |
| 8,880,163 B2 | 11/2014 | Barachant et al. | |
| 8,890,875 B2 | 11/2014 | Jammes et al. | |
| 8,892,479 B2 | 11/2014 | Tan et al. | |
| 9,037,530 B2 | 5/2015 | Tan et al. | |
| D742,272 S | 11/2015 | Bailey et al. | |
| 9,218,574 B2 | 12/2015 | Phillipps et al. | |
| 9,235,934 B2 | 1/2016 | Mandella et al. | |
| 9,240,069 B1 | 1/2016 | Li | |
| 9,278,453 B2 | 3/2016 | Assad | |
| 9,299,248 B2 | 3/2016 | Lake et al. | |
| D756,359 S | 5/2016 | Bailey et al. | |
| 9,367,139 B2 | 6/2016 | Ataee et al. | |
| 9,372,535 B2 | 6/2016 | Bailey et al. | |
| 9,389,694 B2 | 7/2016 | Ataee et al. | |
| 9,408,316 B2 | 8/2016 | Bailey et al. | |
| 9,459,697 B2 | 10/2016 | Bedikian et al. | |
| 9,483,123 B2 | 11/2016 | Aleem et al. | |
| 9,597,015 B2 | 3/2017 | McNames et al. | |
| 9,600,030 B2 | 3/2017 | Bailey et al. | |
| 9,612,661 B2 | 4/2017 | Wagner et al. | |
| 9,613,262 B2 | 4/2017 | Holz | |
| 9,659,403 B1 | 5/2017 | Horowitz | |
| 9,687,168 B2 | 6/2017 | John | |
| 9,696,795 B2 | 7/2017 | Marcolina et al. | |
| 9,720,515 B2 | 8/2017 | Wagner et al. | |
| 9,741,169 B1 | 8/2017 | Holz | |
| 9,766,709 B2 | 9/2017 | Holz | |
| 9,785,247 B1 | 10/2017 | Horowitz et al. | |
| 9,788,789 B2 | 10/2017 | Bailey | |
| 9,864,431 B2 | 1/2018 | Keskin et al. | |
| 9,867,548 B2 | 1/2018 | Le et al. | |
| 9,880,632 B2 | 1/2018 | Ataee et al. | |
| 9,891,718 B2 | 2/2018 | Connor | |
| 10,042,422 B2 | 8/2018 | Morun et al. | |
| 10,070,799 B2 | 9/2018 | Ang et al. | |
| 10,078,435 B2 | 9/2018 | Noel | |
| 10,101,809 B2 | 10/2018 | Morun et al. | |
| 10,152,082 B2 | 12/2018 | Bailey | |
| 10,188,309 B2 | 1/2019 | Morun et al. | |
| 10,199,008 B2 | 2/2019 | Aleem et al. | |
| 10,203,751 B2 | 2/2019 | Keskin et al. | |
| 10,216,274 B2 | 2/2019 | Chapeskie et al. | |
| 10,251,577 B2 | 4/2019 | Morun et al. | |
| 10,310,601 B2 | 6/2019 | Morun et al. | |
| 10,331,210 B2 | 6/2019 | Morun et al. | |
| 10,362,958 B2 | 7/2019 | Morun et al. | |
| 10,409,371 B2 | 9/2019 | Kaifosh et al. | |
| 2003/0144829 A1 | 7/2003 | Geatz et al. | |
| 2003/0171921 A1 | 9/2003 | Manabe et al. | |
| 2003/0184544 A1 | 10/2003 | Prudent | |
| 2004/0092839 A1 | 5/2004 | Shin et al. | |
| 2004/0254617 A1* | 12/2004 | Hemmerling | A61B 7/006 607/48 |
| 2006/0058699 A1* | 3/2006 | Vitiello | A61B 5/1127 600/546 |
| 2007/0172797 A1 | 7/2007 | Hada et al. | |
| 2007/0177770 A1 | 8/2007 | Derchak et al. | |
| 2007/0256494 A1 | 11/2007 | Nakamura et al. | |
| 2007/0285399 A1 | 12/2007 | Lund | |
| 2008/0001735 A1 | 1/2008 | Tran | |
| 2008/0052643 A1 | 2/2008 | Ike et al. | |
| 2008/0214360 A1 | 9/2008 | Stiding et al. | |
| 2008/0221487 A1 | 9/2008 | Zahar et al. | |
| 2009/0082692 A1 | 3/2009 | Hale et al. | |
| 2009/0082701 A1 | 3/2009 | Zohar et al. | |
| 2009/0112080 A1 | 4/2009 | Matthews | |
| 2009/0124881 A1 | 5/2009 | Rytky | |
| 2009/0326406 A1 | 12/2009 | Tan et al. | |
| 2009/0327171 A1 | 12/2009 | Tan et al. | |
| 2010/0030532 A1 | 2/2010 | Arora et al. | |
| 2010/0063794 A1 | 3/2010 | Hernandez-Rebollar | |
| 2010/0106044 A1 | 4/2010 | Linderman | |
| 2010/0280628 A1 | 11/2010 | Sankai | |
| 2010/0292617 A1 | 11/2010 | Lei et al. | |
| 2010/0293115 A1 | 11/2010 | Seyed Momen | |
| 2010/0315266 A1 | 12/2010 | Gunawardana et al. | |
| 2011/0077484 A1 | 3/2011 | Van Slyke et al. | |
| 2011/0092826 A1 | 4/2011 | Lee et al. | |
| 2012/0066163 A1 | 3/2012 | Balls et al. | |
| 2012/0117514 A1 | 5/2012 | Kim et al. | |
| 2012/0188158 A1 | 7/2012 | Tan et al. | |
| 2012/0265480 A1 | 10/2012 | Oshima | |
| 2012/0283526 A1 | 11/2012 | Gommesen et al. | |
| 2013/0077820 A1 | 3/2013 | Marais et al. | |
| 2013/0141375 A1 | 6/2013 | Ludwig et al. | |
| 2013/0207889 A1 | 8/2013 | Chang et al. | |
| 2013/0217998 A1 | 8/2013 | Mahfouz et al. | |
| 2013/0232095 A1 | 9/2013 | Tan et al. | |
| 2013/0310979 A1* | 11/2013 | Herr | B62D 57/032 700/258 |
| 2013/0317382 A1 | 11/2013 | Le | |
| 2013/0317648 A1 | 11/2013 | Assad | |
| 2014/0052150 A1 | 2/2014 | Taylor et al. | |
| 2014/0092009 A1 | 4/2014 | Yen et al. | |
| 2014/0098018 A1 | 4/2014 | Kim et al. | |
| 2014/0196131 A1 | 7/2014 | Lee | |
| 2014/0198034 A1 | 7/2014 | Bailey et al. | |
| 2014/0198035 A1 | 7/2014 | Bailey et al. | |
| 2014/0223462 A1 | 8/2014 | Aimone et al. | |
| 2014/0240103 A1 | 8/2014 | Lake et al. | |
| 2014/0240223 A1 | 8/2014 | Lake et al. | |
| 2014/0245200 A1 | 8/2014 | Holz | |
| 2014/0249397 A1 | 9/2014 | Lake et al. | |
| 2014/0278441 A1 | 9/2014 | Ton et al. | |
| 2014/0297528 A1 | 10/2014 | Agrawal et al. | |
| 2014/0304665 A1 | 10/2014 | Holz | |
| 2014/0334083 A1 | 11/2014 | Bailey | |
| 2014/0344731 A1 | 11/2014 | Holz | |
| 2014/0355825 A1 | 12/2014 | Kim et al. | |

(56) References Cited

U.S. PATENT DOCUMENTS

| | | |
|---|---|---|
| 2014/0365163 A1 | 12/2014 | Jallon |
| 2014/0376773 A1 | 12/2014 | Holz |
| 2015/0006120 A1 | 1/2015 | Sett et al. |
| 2015/0010203 A1 | 1/2015 | Muninder et al. |
| 2015/0025355 A1 | 1/2015 | Bailey et al. |
| 2015/0029092 A1 | 1/2015 | Holz et al. |
| 2015/0035827 A1 | 2/2015 | Yamaoka et al. |
| 2015/0045699 A1 | 2/2015 | Mokaya et al. |
| 2015/0051470 A1 | 2/2015 | Bailey et al. |
| 2015/0057770 A1 | 2/2015 | Bailey et al. |
| 2015/0070270 A1 | 3/2015 | Bailey et al. |
| 2015/0070274 A1 | 3/2015 | Morozov |
| 2015/0084860 A1 | 3/2015 | Aleem et al. |
| 2015/0109202 A1 | 4/2015 | Ataee et al. |
| 2015/0124566 A1 | 5/2015 | Lake et al. |
| 2015/0128094 A1 | 5/2015 | Baldwin et al. |
| 2015/0141784 A1 | 5/2015 | Morun et al. |
| 2015/0148641 A1 | 5/2015 | Morun et al. |
| 2015/0157944 A1 | 6/2015 | Gottlieb |
| 2015/0169074 A1 | 6/2015 | Ataee et al. |
| 2015/0193949 A1 | 7/2015 | Katz et al. |
| 2015/0223716 A1 | 8/2015 | Korkala et al. |
| 2015/0234426 A1 | 8/2015 | Bailey et al. |
| 2015/0261306 A1 | 9/2015 | Lake |
| 2015/0261318 A1 | 9/2015 | Scavezze et al. |
| 2015/0277575 A1 | 10/2015 | Ataee et al. |
| 2015/0289995 A1* | 10/2015 | Wilkinson ............... A61F 2/60 623/27 |
| 2015/0296553 A1 | 10/2015 | DiFranco et al. |
| 2015/0302168 A1 | 10/2015 | De Sapio et al. |
| 2015/0309563 A1 | 10/2015 | Connor |
| 2015/0309582 A1 | 10/2015 | Gupta |
| 2015/0313496 A1 | 11/2015 | Connor |
| 2015/0325202 A1 | 11/2015 | Lake et al. |
| 2015/0346701 A1 | 12/2015 | Gordon et al. |
| 2015/0370326 A1 | 12/2015 | Chapeskie et al. |
| 2015/0370333 A1 | 12/2015 | Ataee et al. |
| 2016/0011668 A1 | 1/2016 | Gilad-Bachrach et al. |
| 2016/0049073 A1 | 2/2016 | Lee |
| 2016/0113587 A1 | 4/2016 | Kothe et al. |
| 2016/0144172 A1 | 5/2016 | Hsueh et al. |
| 2016/0162604 A1 | 6/2016 | Xioli et al. |
| 2016/0187992 A1 | 6/2016 | Yamamoto et al. |
| 2016/0235323 A1 | 8/2016 | Tadi et al. |
| 2016/0262687 A1 | 9/2016 | Imperial |
| 2016/0274758 A1 | 9/2016 | Bailey |
| 2016/0292497 A1 | 10/2016 | Kehtarnavaz et al. |
| 2016/0313798 A1 | 10/2016 | Connor |
| 2016/0313801 A1 | 10/2016 | Wagner et al. |
| 2016/0313899 A1 | 10/2016 | Noel |
| 2016/0350973 A1 | 12/2016 | Shapira et al. |
| 2017/0031502 A1 | 2/2017 | Rosenberg et al. |
| 2017/0035313 A1 | 2/2017 | Hong et al. |
| 2017/0061817 A1 | 3/2017 | Mettler May |
| 2017/0080346 A1 | 3/2017 | Abbas |
| 2017/0090604 A1 | 3/2017 | Barbier |
| 2017/0091567 A1 | 3/2017 | Wang et al. |
| 2017/0119472 A1 | 5/2017 | Herrmann et al. |
| 2017/0123487 A1 | 5/2017 | Hazra et al. |
| 2017/0124816 A1 | 5/2017 | Yang et al. |
| 2017/0188980 A1 | 7/2017 | Ash |
| 2017/0259167 A1 | 9/2017 | Cook et al. |
| 2017/0285848 A1 | 10/2017 | Rosenberg et al. |
| 2017/0296363 A1 | 10/2017 | Yetkin et al. |
| 2017/0301630 A1 | 10/2017 | Nguyen et al. |
| 2017/0308118 A1 | 10/2017 | Ito |
| 2018/0000367 A1 | 1/2018 | Longinotti-Buitoni |
| 2018/0020951 A1 | 1/2018 | Kaifosh et al. |
| 2018/0020978 A1 | 1/2018 | Kaifosh et al. |
| 2018/0024634 A1 | 1/2018 | Kaifosh et al. |
| 2018/0024635 A1 | 1/2018 | Kaifosh et al. |
| 2018/0064363 A1 | 3/2018 | Morun et al. |
| 2018/0067553 A1 | 3/2018 | Morun et al. |
| 2018/0088765 A1 | 3/2018 | Bailey |
| 2018/0095630 A1 | 4/2018 | Bailey |
| 2018/0101289 A1 | 4/2018 | Bailey |
| 2018/0120948 A1 | 5/2018 | Aleem et al. |
| 2018/0140441 A1 | 5/2018 | Poirters |
| 2018/0150033 A1 | 5/2018 | Lake et al. |
| 2018/0153430 A1 | 6/2018 | Ang et al. |
| 2018/0153444 A1 | 6/2018 | Yang et al. |
| 2018/0154140 A1 | 6/2018 | Bouton et al. |
| 2018/0178008 A1* | 6/2018 | Bouton ............... A61B 5/16 |
| 2018/0301057 A1 | 10/2018 | Hargrove et al. |
| 2018/0307314 A1 | 10/2018 | Connor |
| 2018/0321745 A1 | 11/2018 | Morun et al. |
| 2018/0321746 A1 | 11/2018 | Morun et al. |
| 2018/0333575 A1 | 11/2018 | Bouton |
| 2018/0344195 A1 | 12/2018 | Morun et al. |
| 2018/0360379 A1 | 12/2018 | Harrison et al. |
| 2019/0008453 A1* | 1/2019 | Spoof ............... A61B 5/4848 |
| 2019/0025919 A1 | 1/2019 | Tadi et al. |
| 2019/0033967 A1 | 1/2019 | Morun et al. |
| 2019/0038166 A1 | 2/2019 | Tavabi et al. |
| 2019/0076716 A1 | 3/2019 | Chiou et al. |
| 2019/0121305 A1 | 4/2019 | Kaifosh et al. |
| 2019/0121306 A1 | 4/2019 | Kaifosh et al. |
| 2019/0150777 A1 | 5/2019 | Guo et al. |
| 2019/0192037 A1 | 6/2019 | Morun et al. |
| 2019/0212817 A1 | 7/2019 | Kaifosh et al. |
| 2019/0223748 A1 | 7/2019 | Al-Natsheh et al. |
| 2019/0227627 A1 | 7/2019 | Kaifosh et al. |
| 2019/0228330 A1 | 7/2019 | Kaifosh et al. |
| 2019/0228533 A1 | 7/2019 | Giurgica-Tiron et al. |
| 2019/0228579 A1 | 7/2019 | Kaifosh et al. |
| 2019/0228590 A1 | 7/2019 | Kaifosh et al. |
| 2019/0228591 A1 | 7/2019 | Giurgica-Tiron et al. |

FOREIGN PATENT DOCUMENTS

| | | |
|---|---|---|
| CA | 2 939 644 A1 | 8/2015 |
| CN | 1838933 A1 | 9/2006 |
| CN | 105190578 A | 12/2015 |
| CN | 106102504 A | 11/2016 |
| CN | 112074225 A | 12/2020 |
| EP | 2 198 521 B1 | 6/2012 |
| EP | 2 959 394 A1 | 12/2015 |
| EP | 3 104 737 A1 | 12/2016 |
| JP | H05-277080 A | 10/1993 |
| JP | 2005-095561 A | 4/2005 |
| JP | 2010-520561 A | 6/2010 |
| JP | 2016-507851 A | 3/2016 |
| JP | 2017-509386 A | 4/2017 |
| KR | 10-2015-0123254 A | 11/2015 |
| KR | 10-2016-0121552 A | 10/2016 |
| KR | 10-1790147 B1 | 10/2017 |
| WO | 2008/109248 A2 | 9/2008 |
| WO | 2009/042313 A1 | 4/2009 |
| WO | 2014/130871 A1 | 8/2014 |
| WO | 2014/186370 A1 | 11/2014 |
| WO | 2014/194257 A1 | 12/2014 |
| WO | 2014/197443 A1 | 12/2014 |
| WO | 2015/027089 A1 | 2/2015 |
| WO | 2015/073713 A1 | 5/2015 |
| WO | 2015/081113 A1 | 6/2015 |
| WO | 2015/123445 A1 | 8/2015 |
| WO | 2015/199747 A1 | 12/2015 |
| WO | 2016/041088 A1 | 3/2016 |
| WO | 2017/062544 A1 | 4/2017 |
| WO | 2017/120669 A1 | 7/2017 |
| WO | 2017/172185 A1 | 10/2017 |
| WO | 2019/147953 A1 | 8/2019 |

OTHER PUBLICATIONS

International Preliminary Report on Patentability for International Application No. PCT/US2017/043686 dated Feb. 7, 2019.
International Search Report and Written Opinion for International Application No. PCT/US2017/043693 dated Oct. 6, 2017.
International Preliminary Report on Patentability for International Application No. PCT/US2017/043693 dated Feb. 7, 2019.
International Search Report and Written Opinion for International Application No. PCT/US2017/043791 dated Oct. 5, 2017.

(56) References Cited

OTHER PUBLICATIONS

International Preliminary Reporton Patentability for International Application No. PCT/US2017/043791 dated Feb. 7, 2019.
International Search Report and Written Opinion for International Application No. PCT/US2017/043792 dated Oct. 5, 2017.
International Preliminary Report on Patentability for International Application No. PCT/US2017/043792 dated Feb. 7, 2019.
International Search Report and Written Opinion for International Application No. PCT/US2018/056768 dated Jan. 15, 2019.
International Search Report and Written Opinion for International Application No. PCT/US2018/061409 dated Mar. 12, 2019.
International Search Report and Written Opinion for International Application No. PCT/US2018/063215 dated Mar. 21, 2019.
International Search Report and Written Opinion for International Application No. PCT/US2019/015134 dated May 15, 2019.
International Search Report and Written Opinion for International Application No. PCT/US2019/015167 dated May 21, 2019.
International Search Report and Written Opinion for International Application No. PCT/US2019/015174 dated May 21, 2019.
International Search Report and Written Opinion for International Application No. PCT/US2019/015238 dated May 16, 2019.
International Search Report and Written Opinion for International Application No. PCT/US2019/015183 dated May 3, 2019.
International Search Report and Written Opinion for International Application No. PCT/US2019/015180 dated May 16, 2019.
International Search Report and Written Opinion for International Application No. PCT/US2019/015244 dated May 16, 2019.
International Search Report and Written Opinion for International Application No. PCT/US2019/028299 dated Aug. 9, 2019.
Invitation to Pay Additional Fees for International Application No. PCT/US2019/031114 dated Aug. 6, 2019.
International Search Report and Written Opinion for International Application No. PCT/US2019/020065 dated May 16, 2019.
Arkenbout et al., Robust Hand Motion Tracking through Data Fusion of 5DT Data Glove and Nimble VR Kinect Camera Measurements, Sensors, 2015; 15: 31644-71.
Benko et al., Enhancing Input On and Above the Interactive Surface with Muscle Sensing. The ACM International Conference on Interactive Tabletops and Surfaces, ITS '09 ,2009: 93-100.
Boyali et al., Spectral Collaborative Representation based Classification for hand gestures recognition on alectromyography signals, Biomedical Signal Processing and Control, 2016; 24:11-18.
Cheng et al., A Novel Phonology-and Radical-Coded Chinese Sign Language Recognition Framework Using Accelerometer and Surface Electromyography Sensors, Sensors, 2015; 15: 23303-24.
Csapo et al., Evaluation of Human-Myo Gesture Control Capabilities in Continuous Search and Select Operations, 7th IEEE International Conference on Cognitive Infocommunications, 2016; 000415-20.
Davoodi et al., Development of a Physics-Based Target Shooting Game to Train Amputee Users of Multi joint Upper Limb Protheses, Presence, Massachusetts Institute of Technology, 2012; 21(1): 85-95.
Delis et al., Development of a Myoelectric Controller Based on Knee Angle Estimation, Biodevices 2009, International Conference on Biomedical Electronics and Devices, Jan. 17, 2009, 7 pages.
Diener et al., Direct conversion from facial myoelectric signals to speech using Deep Neural Networks, 2015 International Joint Conference on Neural Networks (IJCNN), Oct. 1, 2015, 7 pages.
Ding et al., HMM with improved feature extraction-based feature parameters for identity recognition of gesture command operators by using a sensed Kinect-data stream, Neurocomputing, 2017; 262: 108-19.
Farina et al., Man/machine interface based on the discharge timings of spinal motor neurons after targeted muscle reinnervation, Nature, Biomedical Engineering, 2017; 1:1-12.
Favorskay A et al., Localization and Recognition of Dynamic Hand Gestures Based on Hierarchy of Manifold Classifiers, International Archives of the Photogrammetry, Remote Sensing and Spatial Information Sciences, 2015; XL-5/W6:1-8.

Gallina et al., Surface EMG Biofeedback. Surface Electromyography: Physiology, Engineering, and Applications, 2016:485-500.
Gopura et al., A Human Forearm and wrist motion assist exoskeleton robot with EMG-based fuzzy-neuro control, Proceedings of the 2nd IEEE/RAS-EMBS International Conference on Biomedial Robotics and Biomechatronics, Oct. 19-22, 2008, 6 pages.
Hauschild et al., A Virtual Reality Environment for Designing and Fitting Neural Prosthetic Limbs, IEEE Transactions on Neural Systems and Rehabilitation Engineering, 2007; 15(1):9-15.
Jiang, Purdue University Graduate School Thesis/Dissertation Acceptance, Graduate School Form 30, Updated Jan. 15, 2015, 24 pages.
Kawaguchi et al., Estimation of Finger Joint Angles Based on Electromechanical Sensing of Wrist Shape, IEEE Transactions on Neural Systems and Rehabilitation Engineering, 2017; 25(9): 1409-18.
Kim et al., Real-Time Human Pose Estimation and Gesture Recognition from Depth Images Using Superpixels and SVM Classifier, Sensors, 2015; 15: 12410-27.
Koerner, Design and Characterization of the Exo-Skin Haptic Device: A Novel Tendon Actuated Textile Hand Exoskeleton. 2017, 5 pages.
Lee et al., Motion and Force Estimation System of Human Fingers. Journal of Institute of Control, Robotics and Systems. 2011; 17(10): 1014-1020.
Li et al., Motor Function Evaluation of Hemiplegic Upper-Extremities Using Data Fusion from Wearable Inertial and Surface EMG Sensors, Sensors, MDPI. 2017; 17(582):1-17.
Lopes et al., Hand/arm gesture segmentation by motion using IMU and EMG sensing, ScienceDirect, Elsevier, Procedia Manufacturing, 2017; 11:107-13.
Martin et al., A Novel Approach of Prosthetic Arm Control using Computer Vision, Biosignals, and Motion Capture, IEEE, 2014, 5 pages.
McIntee, A Task Model of Free-Space Movement-Based Gestures, Dissertation, Graduate Faculty of North Carolina State University, Computer Science, 2016, 129 pages.
Mendes et al., Sensor Fusion and Smart Sensor in Sports and Biomedical Applications, Sensors, 2016; 16(1569):1-31.
Naik et al., Source Separation and Identification issues in bio signals: A solution using Blind source seperation, Intech, 2009, 23 pages.
Naik et al., Subtle Hand gesture identification for HCI using Temporal Decorrelation Source Separation BSS of surface EMG, Digital Image Computing Techniques and Applications, IEEE Computer Society, 2007; 30-7.
Megro et al., Multi-channel intramuscular and surface EMG decomposition by convolutive blind source separation, Journal of Neural Engineering, 2016; 13: 1-17.
Saponas et al., "Making Muscle-Computer Interfaces More Practical," CHI 2010, Brauns and Brawn, Apr. 10-15, 2010, pp. 851-854.
Saponas et al., Demonstrating the Feasibility of Using Forearm Electromyography for Muscle-Computer Interfaces, CHI 2008 Proceedings. Physiological Sensing for Input, 2008: 515-24.
Non-Final Office Action received for U.S. Appl. No. 16/258,279 dated Jun. 13, 2019, 38 pages.
Final Office Action received for U.S. Appl. No. 16/258,279 dated Dec. 18, 2019, 45 pages.
Notice of Allowance received for U.S. Appl. No. 16/258,279 dated May 18, 2020, 42 pages.
Saponas et al., Enabling Always-Available Input with Muscle-Computer Interfaces, UIST '09, 2009: 167-76.
Sartori et al., Neural Data-Driven Musculoskeletal Modeling for Personalized Neurorehabilitation Technologies, EEE Transactions on Biomedical Engineering.2016; 63(5): 879-93.
Sauras-Perez et al., A Voice and Pointing Gesture Interaction System for Supporting Human Spontaneous Decisions in Autonomous Cars, Clemson University, All Dissertations, 2017, 174 pages.
Shen et al., I am a Smartwatch and I can Track my User's Arm, University of Illinois at Urbana-Champaign, MobiSys'16, 12 pages.
Son et al., Evaluating the utility of two gestural discomfort evaluation methods, PLOS One, 2017, 21 pages.

(56) References Cited

OTHER PUBLICATIONS

Strbac et al., Microsoft Kinect-Based Artificial Perception System for Control of Functional Electrical Stimulation Assisted Grasping, Hindawi Publishing Corporation, BioMed Research International, 2014, 13 pages.

Torres, Myo Gesture Control Armband, PCMag, Https://www.pcmag.com/article2/0,2817,2485462,00.asp, 2015, 9 pages.

Valero-Cuevas et al., Computational Models for Neuromuscular Function, NIH Public Access Author Manuscript, Jun. 16, 2011, 52 pages.

Wodzinski et al., Sequential Classification of Palm Gestures Based on A* Algorithm and MLP Neural Network for Quadrocopter Control. Metrol. Meas. Syst., 2017; 24(2): 265-76.

Xue et al., Multiple Sensors Based Hand Motion Recognition Using Adaptive Directed Acyclic Graph, Applied Sciences, MDPI, 2017; 7(358): 1-14.

Yang et al., Surface EMG based handgrip force predictions using gene expression programming, Neurocomputing, 2016; 207: 568-579.

Non-Final Office Action received for U.S. Appl. No. 16/258,279 dated Nov. 27, 2020, 44 pages.

Final Office Action received for U.S. Appl. No. 16/258,279 dated Feb. 19, 2021, 58 pages.

Extended European Search Report received for European Patent Application Serial No. 19744404.5 dated Mar. 29, 2021, 11 pages.

International Preliminary Report on Patentability received for PCT Application Serial No. PCT/US2019/015174 dated Aug. 6, 2020, 07 pages.

\* cited by examiner

SYSTEMS AND METHODS FOR MITIGATING NEUROMUSCULAR SIGNAL ARTIFACTS

CROSS REFERENCE TO RELATED APPLICATIONS

This application is a continuation-in-part of U.S. application Ser. No. 16/258,279, filed 25 Jan. 2019, which claims the benefit of U.S. Provisional Application No. 62/621,829, filed on 25 Jan. 2018. This application also claims the benefit of U.S. Provisional Application No. 62/841,061, filed 30 Apr. 2019. The disclosures of each of these applications are incorporated, in their entirety, by this reference.

BRIEF DESCRIPTION OF THE DRAWINGS

The accompanying drawings illustrate a number of exemplary embodiments and are a part of the specification. Together with the following description, these drawings demonstrate and explain various principles of the present disclosure.

Figure 1:
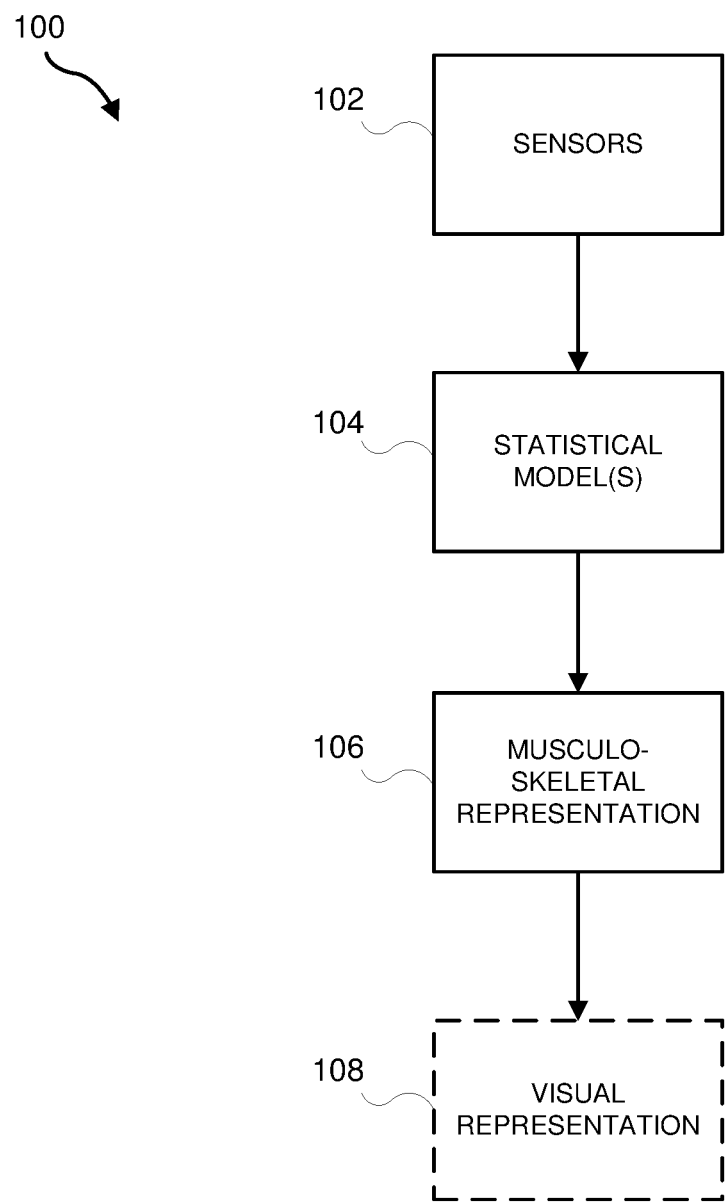
FIG. 1 is a schematic diagram of a computer-based system for generating a musculoskeletal representation based on neuromuscular sensor data in accordance with some embodiments of the technology described herein.

Throughout the drawings, identical reference characters and descriptions indicate similar, but not necessarily identical, elements. While the exemplary embodiments described herein are susceptible to various modifications and alternative forms, specific embodiments have been shown by way of example in the drawings and will be described in detail herein. However, the exemplary embodiments described herein are not intended to be limited to the particular forms disclosed. Rather, the present disclosure covers all modifications, equivalents, and alternatives falling within the scope of the appended claims.

DETAILED DESCRIPTION OF EXEMPLARY EMBODIMENTS

Sensors mounted on wearable devices are subjected to a number of conditions that may affect the quality of sensed signals. For instance, in the case of some neuromuscular sensors, sensed signals can be distorted by, for example, ambient electromagnetic radiation, imperfect contact between sensors (e.g., electrodes) and skin, and crosstalk resulting from electromagnetic interference. For some applications, high-fidelity neuromuscular sensor data may be desirable. For example, in an extended reality (XR) context (e.g., with virtual reality (VR) systems, augmented reality (AR) systems, and/or mixed reality systems), applications that use neuromuscular data to generate visualizations of a user's hand in real time or that use neuromuscular data to provide gesture-based input may rely on high-fidelity data in order to improve a user's sense of immersion and overall experience.

As will be described in greater detail below, systems and methods described herein may improve the fidelity of sensor data from wearable devices by selectively activating and/or differentially pairing sensors based on real-time conditions. For example, these systems and methods may selectively activate and/or differentially pair specific sensors based on real-time evaluations of sensor performance. In some examples, these systems and methods may selectively activate and/or differentially pair specific sensors for specific tasks (e.g., where a particular sensor pair is predicted to perform well producing sensor data for certain types of muscular activation and/or during certain types of movement). In this manner, a sensor-equipped wearable device may provide reliable neuromuscular sensor data even through a wide range of movements and under a wide range of conditions, thereby improving user experience and immersion for applications such as XR applications.

By improving the output of neuromuscular data provided by a wearable device, the systems and methods described herein may improve the functioning of the wearable device and of associated systems (e.g., XR systems). In addition, by selectively activating sensors, these systems and methods may reduce consumption of computational resources of the wearable device and/or associated systems, thereby improving the functioning of the wearable device and/or associated systems. In some examples, selectively activating sensors may reduce power consumption, thereby potentially extending battery life of the wearable device and/or associated systems. These systems and methods therefore represent an advancement in the fields of computing, wearable devices, neuromuscular sensing, and extended reality.

In some examples, systems and methods described herein may use neuromuscular data gathered from a wearable device with dynamically configured sensors to measure and/or model human anatomy (e.g., generate a musculoskeletal representation). Data from the neuromuscular sensors may be applied alone or combined with other sources, such as camera data.

In some examples, systems and methods described herein may predict information about the positioning and movements of portions of a user's arm and/or hand represented as a multi-segment articulated rigid body system with joints connecting the multiple segments of the rigid body system. Signals recorded by wearable neuromuscular sensors placed at locations on the user's body may be provided as input to an inference model trained to predict estimates of the position (e.g., absolute position, relative position, orientation) and/or forces associated with a plurality of rigid segments in a computer-based musculoskeletal representation associated with a hand when a user performs one or more movements. The position information and/or force information associated with segments of a musculoskeletal representation associated with a hand is referred to herein as a "handstate" of the musculoskeletal representation. In some examples, as a user performs different movements, a trained inference model may interpret neuromuscular signals recorded by the wearable neuromuscular sensors into position and force estimates (handstate information) that are used to update the musculoskeletal representation. As the neuromuscular signals are continuously recorded, the musculoskeletal representation is updated in real time (or near real time) and a visual representation of a hand (e.g., within a virtual reality environment) is optionally rendered based on the current handstate estimates.

Due to imperfect neuromuscular sensor data, the estimated handstate output may be noisy, inaccurate, and/or manifest discontinuities. Inaccurate handstate output within a virtual environment may break immersion as a virtual representation of a hand appears unnatural and/or to lack correspondence with the user's actual movements. In addition, where handstate is used for gesture-based input, inaccurate handstate output may interfere with the user's ability to successfully perform gesture-based input.

Accordingly, systems and methods described herein may address issues, such as unreliable neuromuscular sensor data, otherwise observable in the output from a trained inference model. For example, these systems and methods may dynamically configure sensor usage within a wearable device to select sensors (e.g., differential sensor pairs) that will provide more reliable sensor data (e.g., based on specific tasks, such as gathering neuromuscular sensor data for a certain class of movements; and/or based on current conditions, such as poor sensor contact with the skin and/or interfering signals).

All or portions of the human musculoskeletal system can be modeled as a multi-segment articulated rigid body system, with joints forming the interfaces between the different segments and joint angles defining the spatial relationships between connected segments in the model. Constraints on the movement at the joints are governed by the type of joint connecting the segments and the biological structures (e.g., muscles, tendons, ligaments) that restrict the range of movement at the joint. For example, the shoulder joint connecting the upper arm to the torso and the hip joint connecting the upper leg to the torso are ball and socket joints that permit extension and flexion movements as well as rotational movements. By contrast, the elbow joint connecting the upper arm and the forearm and the knee joint connecting the upper leg and the lower leg allow for a more limited range of motion. As described herein, a multi-segment articulated rigid body system is used to model portions of the human musculoskeletal system. However, it should be appreciated that some segments of the human musculoskeletal system (e.g., the forearm), though approximated as a rigid body in the articulated rigid body system, may include multiple rigid structures (e.g., the ulna and radius bones of the forearm) that provide for more complex movement within the segment that is not explicitly considered by the rigid body model. Accordingly, a model of an articulated rigid body system for use with some embodiments of the technology described herein may include segments that represent a combination of body parts that are not strictly rigid bodies.

In kinematics, rigid bodies are objects that exhibit various attributes of motion (e.g., position, orientation, angular velocity, acceleration). Knowing the motion attributes of one segment of the rigid body enables the motion attributes for other segments of the rigid body to be determined based on constraints in how the segments are connected. For example, the hand may be modeled as a multi-segment articulated body with the joints in the wrist and each finger forming the interfaces between the multiple segments in the model. In some embodiments, movements of the segments in the rigid body model can be simulated as an articulated rigid body system in which position (e.g., actual position, relative position, or orientation) information of a segment relative to other segments in the model are predicted using a trained statistical model, as described in more detail below.

The portion of the human body approximated by a musculoskeletal representation, as described herein as one non-limiting example, is a hand or a combination of a hand with one or more arm segments and the information used to describe a current state of the positional relationships between segments and force relationships for individual segments or combinations of segments in the musculoskeletal representation is referred to herein as the handstate of the musculoskeletal representation. It may be appreciated, however, that the techniques described herein are also applicable to musculoskeletal representations of portions of the body other than the hand including, but not limited to, an arm, a leg, a foot, a torso, a neck, or any combination of the foregoing.

FIG. 1 illustrates a system 100 in accordance with some embodiments. The system includes a plurality of sensors 102 configured to record signals resulting from the movement of portions of a human body. Sensors 102 may include autonomous sensors. As used herein, the term "autonomous sensors" refers to sensors configured to measure the movement of body segments without requiring the use of external devices. In some embodiments, sensors 102 may also include non-autonomous sensors in combination with autonomous sensors. As used herein, the term "non-autonomous sensors" refers to sensors configured to measure the movement of body segments using external devices. Examples of external devices that include non-autonomous sensors include, but are not limited to, wearable (e.g. body-mounted) cameras, global positioning systems, and laser scanning systems.

Autonomous sensors may include a plurality of neuromuscular sensors configured to record signals arising from neuromuscular activity in skeletal muscle of a human body. The term "neuromuscular activity" as used herein refers to neural activation of spinal motor neurons that innervate a muscle, muscle activation, muscle contraction, or any combination of the neural activation, muscle activation, and muscle contraction. Neuromuscular sensors may include one or more electromyography (EMG) sensors, one or more mechanomyography (MMG) sensors, one or more sonomyography (SMG) sensors, a combination of two or more types of EMG sensors, MMG sensors, and SMG sensors, and/or one or more sensors of any suitable type that are configured to detect neuromuscular signals. In some embodiments, the plurality of neuromuscular sensors may be used to sense muscular activity related to a movement of the part of the body controlled by muscles from which the neuromuscular sensors are arranged to sense the muscle activity. Spatial information (e.g., position and/or orientation information) and force information describing the movement may be predicted based on the sensed neuromuscular signals as the user moves over time.

Autonomous sensors may include one or more Inertial Measurement Units (IMUs), which measure a combination of physical aspects of motion, using, for example, an accelerometer, a gyroscope, a magnetometer, or any combination of one or more accelerometers, gyroscopes and magnetometers. In some embodiments, IMUs may be used to sense information about the movement of the part of the body on which the IMU is attached and information derived from the sensed data (e.g., position and/or orientation information) may be tracked as the user moves over time. For example, one or more IMUs may be used to track movements of portions of a user's body proximal to the user's torso relative to the sensor (e.g., arms, legs) as the user moves over time.

In embodiments that include at least one IMU and a plurality of neuromuscular sensors, the IMU(s) and neuromuscular sensors may be arranged to detect movement of different parts of the human body. For example, the IMU(s) may be arranged to detect movements of one or more body segments proximal to the torso (e.g., an upper arm), whereas the neuromuscular sensors may be arranged to detect movements of one or more body segments distal to the torso (e.g., a forearm or wrist). It should be appreciated, however, that autonomous sensors may be arranged in any suitable way, and embodiments of the technology described herein are not limited based on the particular sensor arrangement. For example, in some embodiments, at least one IMU and a plurality of neuromuscular sensors may be co-located on a body segment to track movements of body segment using different types of measurements. In one implementation described in more detail below, an IMU sensor and a plurality of EMG sensors are arranged on a wearable device configured to be worn around the lower arm or wrist of a user. In such an arrangement, the IMU sensor may be configured to track movement information (e.g., positioning and/or orientation over time) associated with one or more arm segments, to determine, for example whether the user has raised or lowered their arm, whereas the EMG sensors may be configured to determine movement information associated with wrist or hand segments to determine, for example, whether the user has an open or closed hand configuration.

Each of the autonomous sensors includes one or more sensing components configured to sense information about a user. In the case of IMUs, the sensing components may include one or more accelerometers, gyroscopes, magnetometers, or any combination thereof to measure characteristics of body motion, examples of which include, but are not limited to, acceleration, angular velocity, and sensed magnetic field around the body. In the case of neuromuscular sensors, the sensing components may include, but are not limited to, electrodes configured to detect electric potentials on the surface of the body (e.g., for EMG sensors) vibration sensors configured to measure skin surface vibrations (e.g., for MMG sensors), and acoustic sensing components configured to measure ultrasound signals (e.g., for SMG sensors) arising from muscle activity.

In some embodiments, the output of one or more of the sensing components may be processed using hardware signal processing circuitry (e.g., to perform amplification, filtering, and/or rectification). In other embodiments, at least some signal processing of the output of the sensing components may be performed in software. Thus, signal processing of autonomous signals recorded by the autonomous sensors may be performed in hardware, software, or by any suitable combination of hardware and software, as aspects of the technology described herein are not limited in this respect.

In some embodiments, the recorded sensor data may be processed to compute additional derived measurements that are then provided as input to a statistical model, as described in more detail below. For example, recorded signals from an IMU sensor may be processed to derive an orientation signal that specifies the orientation of a rigid body segment over time. Autonomous sensors may implement signal processing using components integrated with the sensing components, or at least a portion of the signal processing may be performed by one or more components in communication with, but not directly integrated with the sensing components of the autonomous sensors.

In some embodiments, at least some of the plurality of autonomous sensors are arranged as a portion of a wearable device configured to be worn on or around part of a user's body. For example, in one non-limiting example, an IMU sensor and a plurality of neuromuscular sensors are arranged circumferentially around an adjustable and/or elastic band such as a wristband or armband configured to be worn around a user's wrist or arm. Alternatively, at least some of the autonomous sensors may be arranged on a wearable patch configured to be affixed to a portion of the user's body. In some embodiments, multiple wearable devices, each having one or more IMUS and/or neuromuscular sensors included thereon, may be used to predict musculoskeletal position information for movements that involve multiple parts of the body.

In some embodiments, sensors 102 only include a plurality of neuromuscular sensors (e.g., EMG sensors). In other embodiments, sensors 102 include a plurality of neuromuscular sensors and at least one "auxiliary" sensor configured to continuously record a plurality of auxiliary signals. Examples of auxiliary sensors include, but are not limited to, other autonomous sensors such as IMU sensors, and non-autonomous sensors such as an imaging device (e.g., a camera), a radiation-based sensor for use with a radiation-generation device (e.g., a laser-scanning device), or other types of sensors such as a heart-rate monitor.

System 100 also includes one or more computer processors (not shown in FIG. 1) programmed to communicate with sensors 102. For example, signals recorded by one or more of the sensors may be provided to the processor(s), which may be programmed to execute one or more machine learning techniques that process signals output by the sensors 102 to train one or more statistical models 104, and the trained (or retrained) statistical model(s) 104 may be stored for later use in generating a musculoskeletal representation 106, as described in more detail below. Non-limiting examples of statistical models that may be used in accordance with some embodiments to predict handstate information based on recorded signals from sensors 102 are discussed in more detail below with regard to FIG. 5.

System 100 also optionally includes a display controller configured to display a visual representation 108 (e.g., of a hand). As discussed in more detail below, one or more computer processors may implement one or more trained statistical models configured to predict handstate information based, at least in part, on signals recorded by sensors 102. The predicted handstate information is used to update the musculoskeletal representation 106, which is then optionally used to render a visual representation 108 based on the updated musculoskeletal representation incorporating the current handstate information. Real-time reconstruction of the current handstate and subsequent rendering of the visual representation reflecting the current handstate information in the musculoskeletal model may provide visual feedback to the user about the effectiveness of the trained statistical model to accurately represent an intended handstate. Not all embodiments of system 100 include components configured to render a visual representation. For example, in some embodiments, handstate estimates output from the trained statistical model and a corresponding updated musculoskeletal representation are used to determine a state of a user's hand (e.g., in a virtual reality environment) even though a visual representation based on the updated musculoskeletal representation is not rendered (e.g., for interacting with virtual objects in a virtual environment in the absence of a virtually-rendered hand).

In some embodiments, a computer application configured to simulate a virtual reality environment may be instructed to display a visual representation of the user's hand. Positioning, movement, and/or forces applied by portions of the hand within the virtual reality environment may be displayed based on the output of the trained statistical model(s). The visual representation may be dynamically updated based on current reconstructed handstate information as continuous signals are recorded by the sensors 102 and processed by the trained statistical model(s) 104 to provide an updated computer-generated representation of the user's movement and/or exerted force that is updated in real-time.

As discussed above, some embodiments are directed to using a statistical model for predicting musculoskeletal information based on signals recorded from wearable autonomous sensors. The statistical model may be used to predict the musculoskeletal position information without having to place sensors on each segment of the rigid body that is to be represented in the computer-generated musculoskeletal representation. As discussed briefly above, the types of joints between segments in a multi-segment articulated rigid body model constrain movement of the rigid body. Additionally, different individuals tend to move in characteristic ways when performing a task that can be captured in statistical patterns of individual user behavior. At least some of these constraints on human body movement may be explicitly incorporated into statistical models used for prediction in accordance with some embodiments. Additionally or alternatively, the constraints may be learned by the statistical model through training based on ground truth data on the position and exerted forces of the hand and wrist in the context of recorded sensor data (e.g., EMG data). Constraints imposed in the construction of the statistical model are those set by anatomy and the physics of a user's body, while constraints derived from statistical patterns are those set by human behavior for one or more users from which sensor measurements are measured and used to train the statistical model. As described in more detail below, the constraints may comprise part of the statistical model itself being represented by information (e.g., connection weights between nodes) in the model.

As discussed above, some embodiments are directed to using a statistical model for predicting handstate information to enable the generation and/or real-time update of a computer-based musculoskeletal representation. The statistical model may be used to predict the handstate information based on IMU signals, neuromuscular signals (e.g., EMG, MMG, and SMG signals), external device signals (e.g., camera or laser-scanning signals), or a combination of IMU signals, neuromuscular signals, and external device signals detected as a user performs one or more movements.

Relative to tabletop research systems for neuromuscular recording, systems designed for independent use by a non-technical user, including wearable, wireless, and portable neuromuscular recording devices, are more susceptible to recording artifacts. Identifying, mitigating, and accounting for such artifacts is not trivial and doing so effectively enhances the accuracy of systems and methods for estimating the position, movement, and/or forces of a part of a user's body (e.g., hand).

During continuous recording of neuromuscular signals from neuromuscular sensors, artifacts may occasionally appear in the recorded signal data for various reasons including, but not limited to, sensor malfunction and environmental factors such as 60 Hz noise. Providing neuromuscular signals including such artifacts as input to a trained statistical model as described above may result in inaccurate model output estimates (e.g., handstate estimates). Detecting one or more artifacts in the continuously recorded neuromuscular signals in real-time and compensating for the detected artifacts prior to providing the neuromuscular signals as input to the trained statistical model may, however, produce model estimates that more closely represent the user's movements.

Figure 2:
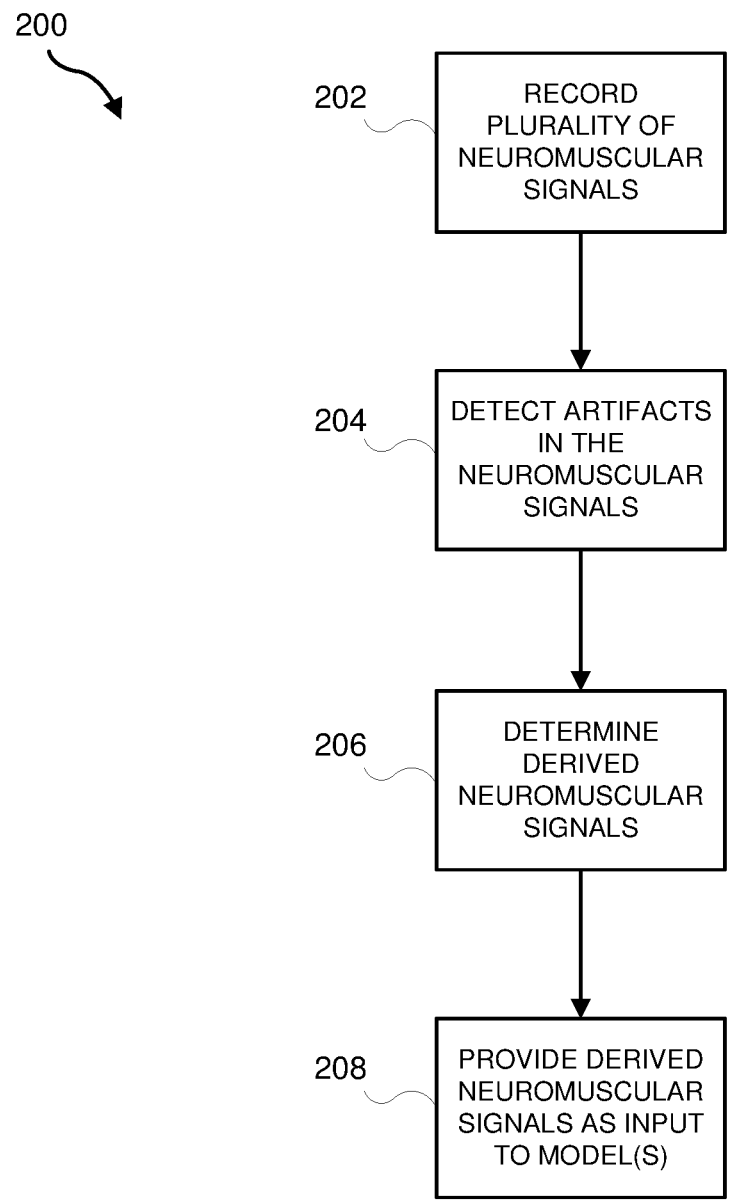
FIG. 2 is flowchart of a process for mitigating neuromuscular signal artifacts in accordance with some embodiments of the technology described herein.

FIG. 2 illustrates a process 200 for detecting and mitigating artifacts in neuromuscular signal data in real-time in accordance with some embodiments. In act 202, a plurality of neuromuscular signals are recorded from a plurality of neuromuscular sensors. Process 200 proceeds to act 204, where the neuromuscular signals are analyzed to detect one or more artifacts in the neuromuscular signals in real-time as the neuromuscular signals are continuously recorded. Process 200 then proceeds to act 206, where derived neuromuscular signals are determined when one or more artifacts are detected in the neuromuscular signals. The derived neuromuscular signals are signals in which the detected artifacts have been mitigated by, for example, processing the signal data to at least partially remove the artifact(s) (e.g., via a filter or other suitable technique as described below), replacing at least some of the signal data with other signal data, or replacing the signal data with an average of signal data from neighboring sensors (as described below). Examples of determining derived neuromuscular signals are discussed in further detail below. Process 200 then proceeds to act 208, where the derived neuromuscular signals are provided as input to a trained statistical model in place of the recorded neuromuscular signals. In some instances, when no artifacts are detected in the neuromuscular signals recorded from particular sensors, the neuromuscular signals from those sensors may be provided as input to the trained statistical model without processing the signals to mitigate artifacts.

Figure 3:
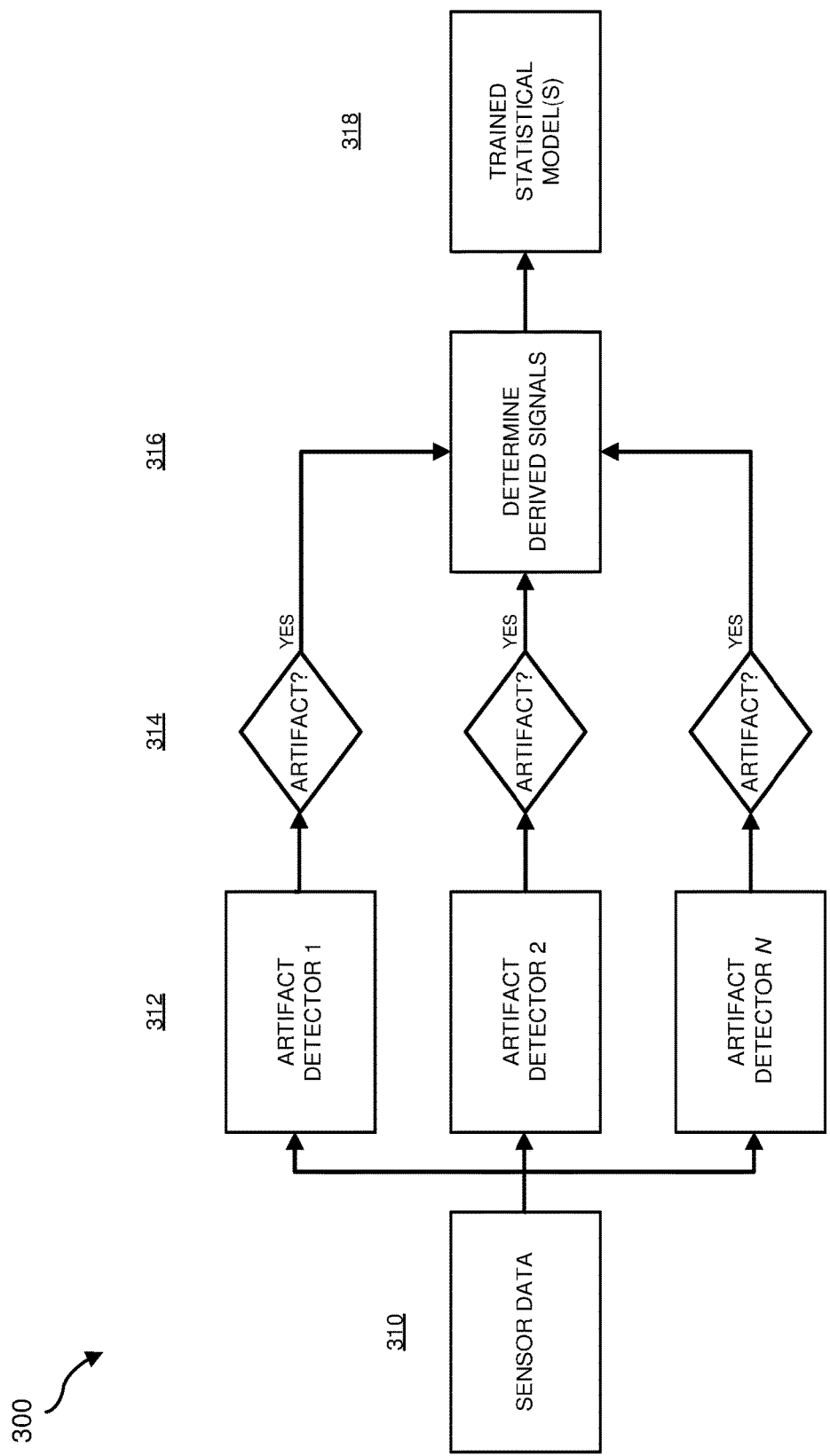
FIG. 3 is a flowchart of a process for mitigating neuromuscular signal artifacts using multiple detector circuits in accordance with some embodiments of the technology described herein.

FIG. 3 illustrates a system architecture 300 for detecting and mitigating artifacts from recorded neuromuscular signals in accordance with some embodiments. Sensor data 310 recorded by a plurality of neuromuscular sensors is analyzed by a plurality of detector circuits 312, each of which is configured to detect a particular type of artifact by analyzing the sensor data. Detector circuits 312 may be implemented using hardware, software, or a combination of hardware and software (as described below). After analyzing the neuromuscular signals, a decision 314 is made as to whether the neuromuscular signals analyzed by the detector circuit 312 include the artifact for which the detector circuit is configured to detect. In some embodiments, decision 314 is made based, at least in part, on a quality metric associated with the neuromuscular signals analyzed by the detector circuit 312. For example, the quality metric may represent a probability (e.g., a confidence level) that the neuromuscular signals include a particular artifact, and it may be determined that the neuromuscular signals include the artifact when the probability is higher than a threshold value. Detector circuits 312 may be configured to process individual channels of neuromuscular sensor data or at least some of the detector circuits 312 may be configured to process neuromuscular sensor data recorded by multiple channels to detect artifacts. In an implementation where each of N detector circuits 312 is configured to process an individual channel of neuromuscular data to detect a particular artifact, the output of the artifact detection process may be a vector of N quality metrics, each of which corresponds to the analysis of the channel data by one of the detector circuits 312. Detector circuits 312 may be configured to detect any suitable signal artifact including, but not limited to, noise artifacts, skin-contact artifacts, skin lift-off artifacts, power line frequency (e.g., 50 Hz, 60 Hz) artifacts, clipped signal artifacts, inactive sensor artifacts, microfriction artifacts, data degeneration artifacts, and artifacts caused by movement of one or more neuromuscular sensors (e.g., the rotation of an armband containing a plurality of neuromuscular sensors that causes the mapping between the location of one or more neuromuscular sensors and the recorded signals of the neuromuscular sensors generated by underlying motor units to change).

When decision 314 indicates that the neuromuscular sensor data includes an artifact detected by a corresponding detector circuit 312, one or more derived neuromuscular signals 316 are determined in which the artifact has been mitigated by, for example, at least partially removing the artifact or replacing the signals with other signals. The derived neuromuscular signals may be determined in any suitable way based on the decisions 314 output from the detector circuits 312 and one or more rules associated with those decisions. In some embodiments, information output from the detector circuits is used to determine whether to process the neuromuscular signals to mitigate the detected artifact(s) or whether to replace the neuromuscular sensor data with other sensor data or data derived from other sensor data.

The decision on whether to process the sensor data or replace the data may be made in any suitable way. In some embodiments, the decision of whether to process or replace the sensor data may be made on a detector circuit by detector circuit basis. For example, for some detector circuits, the neuromuscular signals may always be processed (rather than replaced) to mitigate a detected artifact based on the type of artifact that the detector circuit is configured to detect. For example, if the artifact detected is external 60 Hz noise, the neuromuscular signals may always be processed by filtering rather than being replaced. In other instances, the neuromuscular signals may always be replaced rather than being processed. For example, if the detector circuit is configured to detect artifacts corresponding to a disconnected or malfunctioning sensor, the neuromuscular signals may always be replaced (rather than being processed) with an average (or other metric) of neuromuscular signals from one or more neighboring sensors. In yet other instances, a determination of whether the neuromuscular signals analyzed by a particular detector circuit should be processed or replaced is made based, at least in part, on a quality factor determined as a result of the analysis by the detector circuit. For example, if the quality factor is less than a threshold value or within a first range, the neuromuscular sensor data may be replaced, whereas when the quality factor is greater than a threshold or within a second range, the neuromuscular sensor data may be processed.

In some embodiments, the decision on whether to process neuromuscular signals with detected artifact(s) or replace the neuromuscular signals may be made based on the output of multiple detector circuits. For example, if the detector circuits indicate that multiple artifacts in a particular neuromuscular sensor channel or group of neuromuscular sensors have been detected, it may be determined to replace the neuromuscular signals due to the poor quality of the recorded signals.

When it is determined to process the neuromuscular signals based on the decision 314 for a particular detector circuit 312, the processing may be performed in any suitable way to mitigate the detected artifact. For example, the neuromuscular signals may be filtered or otherwise processed to mitigate the detected artifact. The type of artifact and/or characteristics of the artifact that is detected may inform how the neuromuscular signals are processed. In some implementations the neuromuscular signals may be analyzed to determine one or more characteristics of the artifact by, for example, calculating a power spectrum to determine the frequency characteristics of the artifact, or fitting a generative model of certain artifact types to the neuromuscular signals. After determining the artifact characteristic(s) the neuromuscular signals may be processed to mitigate the artifact. For some types of artifacts (e.g., skin lift-off artifacts), the processing may involve filtering techniques (e.g., a high pass filter above a critical frequency). For other types of artifacts, the processing may involve subtracting at least some estimated artifact behavior from the recorded neuromuscular signals using, for example, a generative model.

When it is determined to replace the neuromuscular signals based on the decision 314 for a particular detector circuit 312 or collection of detector circuits 312, the replacing may be performed in any suitable way to mitigate the detected artifact. For example, if the detected artifact occurs over a relatively short time period, the neuromuscular signal data for a particular sensor may be replaced with signal data from the same sensor recorded at an earlier point in time when the artifact was not present in the signal. Replacing the corrupted signal data (e.g., signal data with detected artifacts) with signal data from the same sensor may be preferred in some instances because the signal data used for replacement has been recorded for neuromuscular activity from the same muscle or muscles as the corrupted signal data. Alternatively, if the detected artifact occurs over a relatively long period of time or if the signal data from the sensor is unusable (e.g., if the sensor has been disconnected or has contact issues), the signal data may be replaced with signal data recorded by other sensors. For example, the signal data may be replaced based on signal data recorded by one or more sensors arranged adjacent to the sensor having the corrupted data. In some embodiments, the signal data for the corrupted sensor may be replaced with an average of signal data from two or more neighboring sensors to the corrupted sensor. For example, the two or more neighboring sensors may be arranged next to or near the corrupted sensor on a wearable device that includes the plurality of neuromuscular sensors. In some embodiments, the average of signal data may be a weighted average of signal data, where the weights are determined in any suitable way. In some embodiments, the weight for data recorded by a neuromuscular sensor with an artifact may be set to zero such that data from that sensor is not considered. In some embodiments, signal data from a neuromuscular sensor with an artifact may be imputed based on neuromuscular signal data derived from historical data of neuromuscular sensors in an array of neuromuscular sensors that are not experiencing an artifact. In certain embodiments, imputed signal data may be user-specific or based on data from a population of users. Signal data from a neuromuscular sensor experiencing an artifact may be inferred and the inference may comprise raw signal data or processed signal data (e.g., amplitude, cospectrum matrix, or another metric). In some embodiments, the inference about signal data from a neuromuscular sensor experiencing an artifact may be generated based on one or more of: general constraints about the neuromuscular system and human anatomy; personal constraints related to the user's physiology and/or anatomy; and session-specific constraints related to the particular positioning and impedance of a plurality of neuromuscular sensors.

When only a single detector circuit 312 of a plurality of detector circuits detects an artifact in the analyzed neuromuscular signals, the neuromuscular signals may be processed or replaced based on one or more rules specifying how to process/replace data when the artifact is detected by the single detector circuit 312. When multiple detector circuits detect artifacts in the analyzed neuromuscular signals, the neuromuscular signals may be processed or replaced based on one or more rules specifying how to process or replace data when multiple artifacts are detected. For example, the one or more rules may specify a processing hierarchy (or order) based on the detected artifacts such that processing to mitigate certain artifacts is performed prior to processing to mitigate other artifacts. Additionally, the one or more rules may specify that if any of the detector circuits 312 detects an artifact with a quality value less than a particular threshold, the signal data is replaced (rather than processed) regardless of artifacts detected by the other detector circuits 312. Any other rules may alternatively be used, and embodiments are not limited in this respect.

After the derived signals 316 in which the signal artifacts have been mitigated are determined, the derived signals are provided as input to a trained statistical model 318, which in turn is configured to output estimates (e.g., handstate estimates) based on the input signals. It should be appreciated that some neuromuscular signals may be processed/replaced when an artifact is detected, whereas other contemporaneously recorded neuromuscular signals (e.g., from other sensors) may not be processed/replaced when no artifacts are detected, and the combination of unprocessed (for mitigating artifacts) and derived signals may be provided as input to the trained statistical model.

Figure 4:
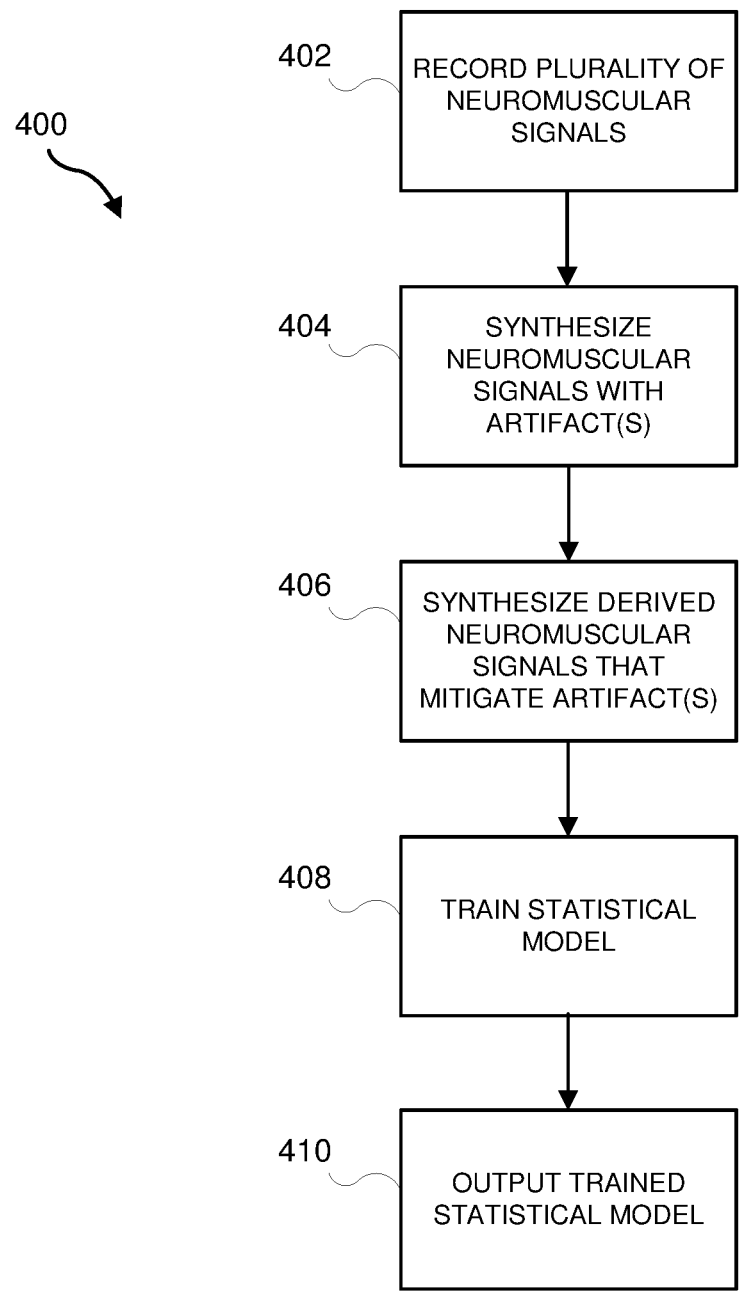
FIG. 4 is a flowchart of a process for training a statistical model using training data determined based on neuromuscular signal data with simulated artifacts in accordance with some embodiments of the technology described herein.

Trained statistical models used in accordance with some embodiments may be trained using training data that makes the model more robust to artifacts in the recorded signals. FIG. 4 illustrates a process 400 for training a statistical model using training data that includes neuromuscular signals associated with artifacts. The artifacts may be recorded as part of the neuromuscular signals or the artifacts may be simulated and added to the recorded neuromuscular signals. Such a trained statistical model when used during runtime may be more robust to artifacts in the recorded neuromuscular signals. Process 400 begins in act 402 where neuromuscular signals are continuously recorded. Process 400 then proceeds to act 404 where neuromuscular signals with one or more artifacts are synthesized by modifying the recorded neuromuscular signals to include characteristics of the artifact. The synthesized neuromuscular signals may be created in any suitable way. For example, noise may be added to the neuromuscular signals to simulate the presence of noise in the recorded signals when used in a particular environment (e.g., an environment in which 60 Hz noise is prevalent). In some embodiments, synthesized neuromuscular signals based on some or all of the types of artifacts detected by the detection circuits described in connection with the architecture of FIG. 3 may be used in act 404. Alternatively, the recorded neuromuscular signals used as training data to train the model may already have artifacts included in the recorded signals, making it unnecessary to simulate the artifacts and add the simulated artifacts into "clean" neuromuscular signals. For example, an armband with a plurality of neuromuscular sensors may be worn loosely in order to generate frequent contact artifacts caused by a neuromuscular sensor transiently losing low-impedance contact with the skin.

Process 400 then proceeds to act 406, where derived neuromuscular signals are synthesized in which the artifacts introduced to the neuromuscular signals in act 404 have been mitigated. Realizing that the mitigation techniques described herein for mitigating signal artifacts may not entirely remove the signal artifacts, inclusion in the training data of synthesized derived neuromuscular signal data that mimics the operation of the mitigation techniques used during runtime results in a trained statistical model that may provide more accurate model estimates.

Process 400 then proceeds to act 408, where the statistical model is trained using training data that includes the synthesized derived neuromuscular signals. Following training, process 400 proceeds to act 410, where the trained statistical model is output for use during runtime as described above in connection with FIGS. 1-3.

In some embodiments, a denoising autoencoder as a component of a statistical model is used to identify and mitigate an artifact. A denoising autoencoder can be implemented by building a statistical model (e.g., a neural network) where input data comprises clean neuromuscular sensor data containing no (or few) artifacts combined with artifacts (e.g., noise), then training the model with the clean neuromuscular sensor data. In this manner, a system or method with a statistical model comprising a denoising autoencoder may provide robustness to neuromuscular artifacts. The artifacts added to the clean neuromuscular sensor data may have a statistical structure consistent with any suitable signal artifact including, but not limited to, noise artifacts, skin-contact artifacts, skin lift-off artifacts, power line frequency (e.g., 50 Hz, 60 Hz) artifacts, clipped signal artifacts, inactive sensor artifacts, microfriction artifacts, data degeneration artifacts, and artifacts caused by movement of one or more neuromuscular sensors (e.g., the rotation of an armband containing a plurality of neuromuscular sensors that causes the mapping between the location of one or more neuromuscular sensors and the recorded signals of the neuromuscular sensors generated by underlying motor units to change).

In some embodiments, simple quality metrics may be derived from the first few principal components of the log power spectra of the neuromuscular sensor data, which tend to be stereotyped across electrodes and between users and recording sessions. For example, linear and quadratic discriminant analysis may account for common causes of aberrant power spectra (e.g., to be able to identify artifacts including but not limited to: motion artifacts (low frequency), contact artifacts (broadband noise), power-line noise (60 Hz), artifacts caused by ground truth data systems that determine the position of a part of the user's body (e.g. joints of the hand), and IMU artifacts). In a variation of this embodiment, cospectral features of multi-channel neuromuscular data may be used to identify artifacts manifesting as correlational information between neuromuscular sensors.

Figure 5:
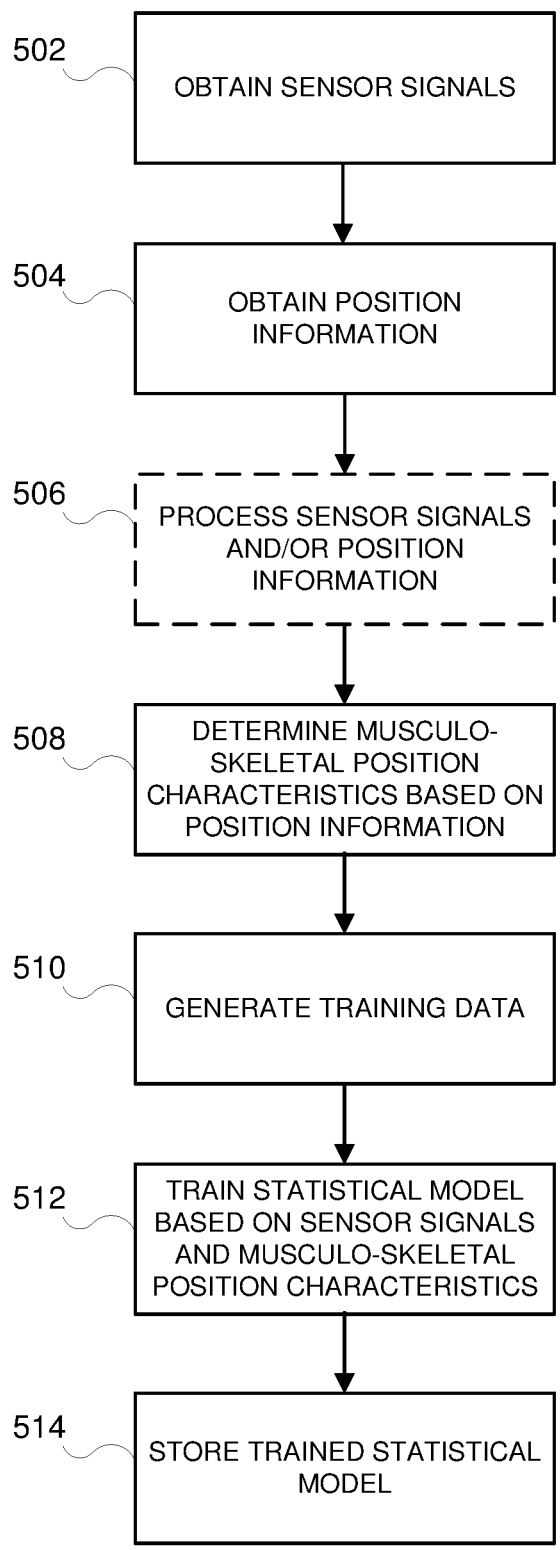
FIG. 5 is a flowchart of an illustrative process for generating a statistical model for predicting musculoskeletal position information using signals recorded from sensors, in accordance with some embodiments of the technology described herein.

FIG. 5 describes a process 500 for generating (sometimes termed "training" herein) a statistical model using signals recorded from sensors 102. Process 500 may be executed by any suitable computing device(s), as aspects of the technology described herein are not limited in this respect. For example, process 500 may be executed by one or more computer processors described with reference to FIGS. 7A and 7B. As another example, one or more acts of process 500 may be executed using one or more servers (e.g., servers included as a part of a cloud computing environment). For example, at least a portion of act 510 relating to training of a statistical model (e.g., a neural network) may be performed using a cloud computing environment.

Process 500 begins at act 502, where a plurality of sensor signals are obtained for one or multiple users performing one or more movements (e.g., typing on a keyboard). In some embodiments, the plurality of sensor signals may be recorded as part of process 500. In other embodiments, the plurality of sensor signals may have been recorded prior to the performance of process 500 and are accessed (rather than recorded) at act 502.

In some embodiments, the plurality of sensor signals may include sensor signals recorded for a single user performing a single movement or multiple movements. The user may be instructed to perform a sequence of movements for a particular task (e.g., opening a door) and sensor signals corresponding to the user's movements may be recorded as the user performs the task he/she was instructed to perform. The sensor signals may be recorded by any suitable number of sensors located in any suitable location(s) to detect the user's movements that are relevant to the task performed. For example, after a user is instructed to perform a task with the fingers of his/her right hand, the sensor signals may be recorded by multiple neuromuscular sensors circumferentially (or otherwise) arranged around the user's lower right arm to detect muscle activity in the lower right arm that give rise to the right hand movements and one or more IMU sensors arranged to predict the joint angle of the user's arm relative to the user's torso. As another example, after a user is instructed to perform a task with his/her leg (e.g., to kick an object), sensor signals may be recorded by multiple neuromuscular sensors circumferentially (or otherwise) arranged around the user's leg to detect muscle activity in the leg that give rise to the movements of the foot and one or more IMU sensors arranged to predict the joint angle of the user's leg relative to the user's torso.

In some embodiments, the sensor signals obtained in act 502 correspond to signals from one type of sensor (e.g., one or more IMU sensors or one or more neuromuscular sensors) and a statistical model may be trained based on the sensor signals recorded using the particular type of sensor, resulting in a sensor-type specific trained statistical model. For example, the obtained sensor signals may comprise a plurality of EMG sensor signals arranged around the lower arm or wrist of a user and the statistical model may be trained to predict musculoskeletal position information for movements of the wrist and/or hand during performance of a task such as grasping and twisting an object such as a doorknob.

In embodiments that provide predictions based on multiple types of sensors (e.g., IMU sensors, EMG sensors, MMG sensors, SMG sensors), a separate statistical model may be trained for each of the types of sensors and the outputs of the sensor-type specific models may be combined to generate a musculoskeletal representation of the user's body. In other embodiments, the sensor signals obtained in act 502 from two or more different types of sensors may be provided to a single statistical model that is trained based on the signals recorded from the different types of sensors. In one illustrative implementation, an IMU sensor and a plurality of EMG sensors are arranged on a wearable device configured to be worn around the forearm of a user, and signals recorded by the IMU and EMG sensors are collectively provided as inputs to a statistical model, as discussed in more detail below.

In some embodiments, the sensor signals obtained in act 502 are recorded at multiple time points as a user performs one or multiple movements. As a result, the recorded signal for each sensor may include data obtained at each of multiple time points. Assuming that n sensors are arranged to simultaneously measure the user's movement information during performance of a task, the recorded sensor signals for the user may comprise a time series of K n-dimensional vectors $\{x_k | 1 \leq k \leq K\}$ at time points $t_1, t_2, \ldots, t_K$ during performance of the movements.

In some embodiments, a user may be instructed to perform a task multiple times and the sensor signals and position information may be recorded for each of multiple repetitions of the task by the user. In some embodiments, the plurality of sensor signals may include signals recorded for multiple users, each of the multiple users performing the same task one or more times. Each of the multiple users may be instructed to perform the task and sensor signals and position information corresponding to that user's movements may be recorded as the user performs (once or repeatedly) the task he/she was instructed to perform. When sensor signals are collected by multiple users which are combined to generate a statistical model, an assumption is that different users employ similar musculoskeletal positions to perform the same movements. Collecting sensor signals and position information from a single user performing the same task repeatedly and/or from multiple users performing the same task one or multiple times facilitates the collection of sufficient training data to generate a statistical model that can accurately predict musculoskeletal position information associated with performance of the task.

In some embodiments, a user-independent statistical model may be generated based on training data corresponding to the recorded signals from multiple users, and as the system is used by a user, the statistical model is trained based on recorded sensor data such that the statistical model learns the user-dependent characteristics to refine the prediction capabilities of the system for the particular user.

In some embodiments, the plurality of sensor signals may include signals recorded for a user (or each of multiple users) performing each of multiple tasks one or multiple times. For example, a user may be instructed to perform each of multiple tasks (e.g., grasping an object, pushing an object, and pulling open a door) and signals corresponding to the user's movements may be recorded as the user performs each of the multiple tasks he/she was instructed to perform. Collecting such data may facilitate developing a statistical model for predicting musculoskeletal position information associated with multiple different actions that may be taken by the user. For example, training data that incorporates musculoskeletal position information for multiple actions may facilitate generating a statistical model for predicting which of multiple possible movements a user may be performing.

As discussed above, the sensor data obtained at act 502 may be obtained by recording sensor signals as each of one or multiple users performs each of one or more tasks one or more multiple times. As the user(s) perform the task(s), position information describing the spatial position of different body segments during performance of the task(s) may be obtained in act 504. In some embodiments, the position information is obtained using one or more external devices or systems that track the position of different points on the body during performance of a task. For example, a motion capture system, a laser scanner, a device to measure mutual magnetic induction, or some other system configured to capture position information may be used. As one non-limiting example, a plurality of position sensors may be placed on segments of the fingers of the right hand and a motion capture system may be used to determine the spatial location of each of the position sensors as the user performs a task such as grasping an object. The sensor data obtained at act 502 may be recorded simultaneously with recording of the position information obtained in act 504. In this example, position information indicating the position of each finger segment over time as the grasping motion is performed is obtained.

Next, process 500 proceeds to act 506, where the sensor signals obtained in act 502 and/or the position information obtained in act 504 are optionally processed. For example, the sensor signals or the position information signals may be processed using amplification, filtering, rectification, or other types of signal processing.

Next, process 500 proceeds to act 508, where musculoskeletal position characteristics are determined based on the position information (as collected in act 504 or as processed in act 506). In some embodiments, rather than using recorded spatial (e.g., x, y, z) coordinates corresponding to the position sensors as training data to train the statistical model, a set of derived musculoskeletal position characteristic values are determined based on the recorded position information, and the derived values are used as training data for training the statistical model. For example, using information about the constraints between connected pairs of rigid segments in the articulated rigid body model, the position information may be used to determine joint angles that define angles between each connected pair of rigid segments at each of multiple time points during performance of a task. Accordingly, the position information obtained in act 504 may be represented by a vector of n joint angles at each of a plurality of time points, where n is the number of joints or connections between segments in the articulated rigid body model.

Next, process 500 proceeds to act 510, where the time series information obtained at acts 502 and 508 is combined to create training data used for training a statistical model at act 510. The obtained data may be combined in any suitable way. In some embodiments, each of the sensor signals obtained at act 502 may be associated with a task or movement within a task corresponding to the musculoskeletal position characteristics (e.g., joint angles) determined based on the positional information recorded in act 504 as the user performed the task or movement. In this way, the sensor signals may be associated with musculoskeletal position characteristics (e.g., joint angles) and the statistical model may be trained to predict that the musculoskeletal representation will be characterized by particular musculoskeletal position characteristics between different body segments when particular sensor signals are recorded during performance of a particular task.

In embodiments comprising sensors of different types (e.g., IMU sensors and neuromuscular sensors) configured to simultaneously record different types of movement information during performance of a task, the sensor data for the different types of sensors may be recorded using the same or different sampling rates. When the sensor data is recorded at different sampling rates, at least some of the sensor data may be resampled (e.g., up-sampled or down-sampled) such that all sensor data provided as input to the statistical model corresponds to time series data at the same time resolution. Resampling at least some of the sensor data may be performed in any suitable way including, but not limited to using interpolation for upsampling and using decimation for downsampling.

In addition to or as an alternative to resampling at least some of the sensor data when recorded at different sampling rates, some embodiments employ a statistical model configured to accept multiple inputs asynchronously. For example, the statistical model may be configured to model the distribution of the "missing" values in the input data having a lower sampling rate. Alternatively, the timing of training of the statistical model occur asynchronously as input from multiple sensor data measurements becomes available as training data.

Next, process 500 proceeds to act 512, where a statistical model for predicting musculoskeletal position information is trained using the training data generated at act 510. The statistical model being trained may take as input a sequence of data sets each of the data sets in the sequence comprising an n-dimensional vector of sensor data. The statistical model may provide output that indicates, for each of one or more tasks or movements that may be performed by a user, the likelihood that the musculoskeletal representation of the user's body will be characterized by a set of musculoskeletal position characteristics (e.g., a set of joint angles between segments in an articulated multi-segment body model). For example, the statistical model may take as input a sequence of vectors $\{x_k | 1 \leq k \leq K\}$ generated using measurements obtained at time points $t_1, t_2, \ldots, t_K$, where the ith component of vector $x_j$ is a value measured by the ith sensor at time $t_j$ and/or derived from the value measured by the ith sensor at time $t_j$. In another non-limiting example, a derived value provided as input to the statistical model may comprise features extracted from the data from all or a subset of the sensors at and/or prior to time $t_j$ (e.g., a covariance matrix, a power spectrum, a combination thereof, or any other suitable derived representation). Based on such input, the statistical model may provide output indicating, a probability that a musculoskeletal representation of the user's body will be characterized by a set of musculoskeletal position characteristics. As one non-limiting example, the statistical model may be trained to predict a set of joint angles for segments in the fingers in the hand over time as a user grasps an object. In this example, the trained statistical model may output, a set of predicted joint angles for joints in the hand corresponding to the sensor input.

In some embodiments, the statistical model may be a neural network and, for example, may be a recurrent neural network. In some embodiments, the recurrent neural network may be a long short-term memory (LSTM) neural network. It should be appreciated, however, that the recurrent neural network is not limited to being an LSTM neural network and may have any other suitable architecture. For example, in some embodiments, the recurrent neural network may be a fully recurrent neural network, a recursive neural network, a variational autoencoder, a Hopfield neural network, an associative memory neural network, an Elman neural network, a Jordan neural network, an echo state neural network, a second order recurrent neural network, and/or any other suitable type of recurrent neural network. In other embodiments, neural networks that are not recurrent neural networks may be used. For example, deep neural networks, convolutional neural networks, and/or feedforward neural networks, may be used.

In some of the embodiments in which the statistical model is a neural network, the output layer of the neural network may provide a set of output values corresponding to a respective set of possible musculoskeletal position characteristics (e.g., joint angles). In this way, the neural network may operate as a non-linear regression model configured to predict musculoskeletal position characteristics from raw or pre-processed sensor measurements. It should be appreciated that, in some embodiments, any other suitable non-linear regression model may be used instead of a neural network, as aspects of the technology described herein are not limited in this respect.

In some embodiments, the neural network can be implemented based on a variety of topologies and/or architectures including deep neural networks with fully connected (dense) layers, Long Short-Term Memory (LSTM) layers, convolutional layers, Temporal Convolutional Layers (TCL), or other suitable type of deep neural network topology and/or architecture. The neural network can have different types of output layers including output layers with logistic sigmoid activation functions, hyperbolic tangent activation functions, linear units, rectified linear units, or other suitable type of nonlinear unit. Likewise, the neural network can be configured to represent the probability distribution over n different classes via, for example, a softmax function or include an output layer that provides a parameterized distribution e.g., mean and variance of a Gaussian distribution.

It should be appreciated that aspects of the technology described herein are not limited to using neural networks, as other types of statistical models may be employed in some embodiments. For example, in some embodiments, the statistical model may comprise a hidden Markov model, a Markov switching model with the switching allowing for toggling among different dynamic systems, dynamic Bayesian networks, and/or any other suitable graphical model having a temporal component. Any such statistical model may be trained at act 512 using the sensor data obtained at act 502.

As another example, in some embodiments, the statistical model may take as input, features derived from the sensor data obtained at act 502. In such embodiments, the statistical model may be trained at act 512 using features extracted from the sensor data obtained at act 502. The statistical model may be a support vector machine, a Gaussian mixture model, a regression-based classifier, a decision tree classifier, a Bayesian classifier, and/or any other suitable classifier, as aspects of the technology described herein are not limited in this respect. Input features to be provided as training data to the statistical model may be derived from the sensor data obtained at act 502 in any suitable way. For example, the sensor data may be analyzed as time series data using wavelet analysis techniques (e.g., continuous wavelet transform, discrete-time wavelet transform, etc.), Fourier-analytic techniques (e.g., short-time Fourier transform, Fourier transform, etc.), and/or any other suitable type of time-frequency analysis technique. As one non-limiting example, the sensor data may be transformed using a wavelet transform and the resulting wavelet coefficients may be provided as inputs to the statistical model.

In some embodiments, at act 512, values for parameters of the statistical model may be estimated from the training data generated at act 510. For example, when the statistical model is a neural network, parameters of the neural network (e.g., weights) may be estimated from the training data. In some embodiments, parameters of the statistical model may be estimated using gradient descent, stochastic gradient descent, and/or any other suitable iterative optimization technique. In embodiments where the statistical model is a recurrent neural network (e.g., an LSTM), the statistical model may be trained using stochastic gradient descent and backpropagation through time. The training may employ a cross-entropy loss function and/or any other suitable loss function, as aspects of the technology described herein are not limited in this respect.

Next, process 500 proceeds to act 514, where the trained statistical model is stored (e.g., in datastore—not shown). The trained statistical model may be stored using any suitable format, as aspects of the technology described herein are not limited in this respect. In this way, the statistical model generated during execution of process 500 may be used at a later time, for example, to predict musculoskeletal position information (e.g., joint angles) for a given set of input sensor data, as described below.

In some embodiments, sensor signals are recorded from a plurality of sensors (e.g., arranged on or near the surface of a user's body) that record activity associated with movements of the body during performance of a task. The recorded signals may be optionally processed and provided as input to a statistical model trained using one or more techniques described above in connection with FIG. 5. In some embodiments that continuously record autonomous signals, the continuously recorded signals (raw or processed) may be continuously or periodically provided as input to the trained statistical model for prediction of musculoskeletal position information (e.g., joint angles) for the given set of input sensor data. As discussed above, in some embodiments, the trained statistical model is a user-independent model trained based on autonomous sensor and position information measurements from a plurality of users. In other embodiments, the trained model is a user-dependent model trained on data recorded from the individual user from which the data associated with the sensor signals is also acquired.

After the trained statistical model receives the sensor data as a set of input parameters, the predicted musculoskeletal position information is output from the trained statistical model. As discussed above, in some embodiments, the predicted musculoskeletal position information may comprise a set of musculoskeletal position information values (e.g., a set of joint angles) for a multi-segment articulated rigid body model representing at least a portion of the user's body. In other embodiments, the musculoskeletal position information may comprise a set of probabilities that the user is performing one or more movements from a set of possible movements.

In some embodiments, after musculoskeletal position information is predicted, a computer-based musculoskeletal representation of the user's body is generated based, at least in part, on the musculoskeletal position information output from the trained statistical model. The computer-based musculoskeletal representation may be generated in any suitable way. For example, a computer-based musculoskeletal model of the human body may include multiple rigid body segments, each of which corresponds to one or more skeletal structures in the body. For example, the upper arm may be represented by a first rigid body segment, the lower arm may be represented by a second rigid body segment the palm of the hand may be represented by a third rigid body segment, and each of the fingers on the hand may be represented by at least one rigid body segment (e.g., at least fourth-eighth rigid body segments). A set of joint angles between connected rigid body segments in the musculoskeletal model may define the orientation of each of the connected rigid body segments relative to each other and a reference frame, such as the torso of the body. As new sensor data is measured and processed by the statistical model to provide new predictions of the musculoskeletal position information (e.g., an updated set of joint angles), the computer-based musculoskeletal representation of the user's body may be updated based on the updated set of joint angles determined based on the output of the statistical model. In this way the computer-based musculoskeletal representation is dynamically updated in real-time as sensor data is continuously recorded.

The computer-based musculoskeletal representation may be represented and stored in any suitable way, as embodiments of the technology described herein are not limited with regard to the particular manner in which the representation is stored. Additionally, although referred to herein as a "musculoskeletal" representation, to reflect that muscle activity may be associated with the representation in some embodiments, as discussed in more detail below, it should be appreciated that some musculoskeletal representations used in accordance with some embodiments may correspond to skeletal structures, muscular structures or a combination of skeletal structures and muscular structures in the body.

In some embodiments, direct measurement of neuromuscular activity and/or muscle activity underlying the user's movements may be combined with the generated musculoskeletal representation. Measurements from a plurality of sensors placed at locations on a user's body may be used to create a unified representation of muscle recruitment by superimposing the measurements onto a dynamically posed skeleton. In some embodiments, muscle activity sensed by neuromuscular sensors and/or information derived from the muscle activity (e.g., force information) may be combined with the computer-generated musculoskeletal representation in real time.

Figure 6A:
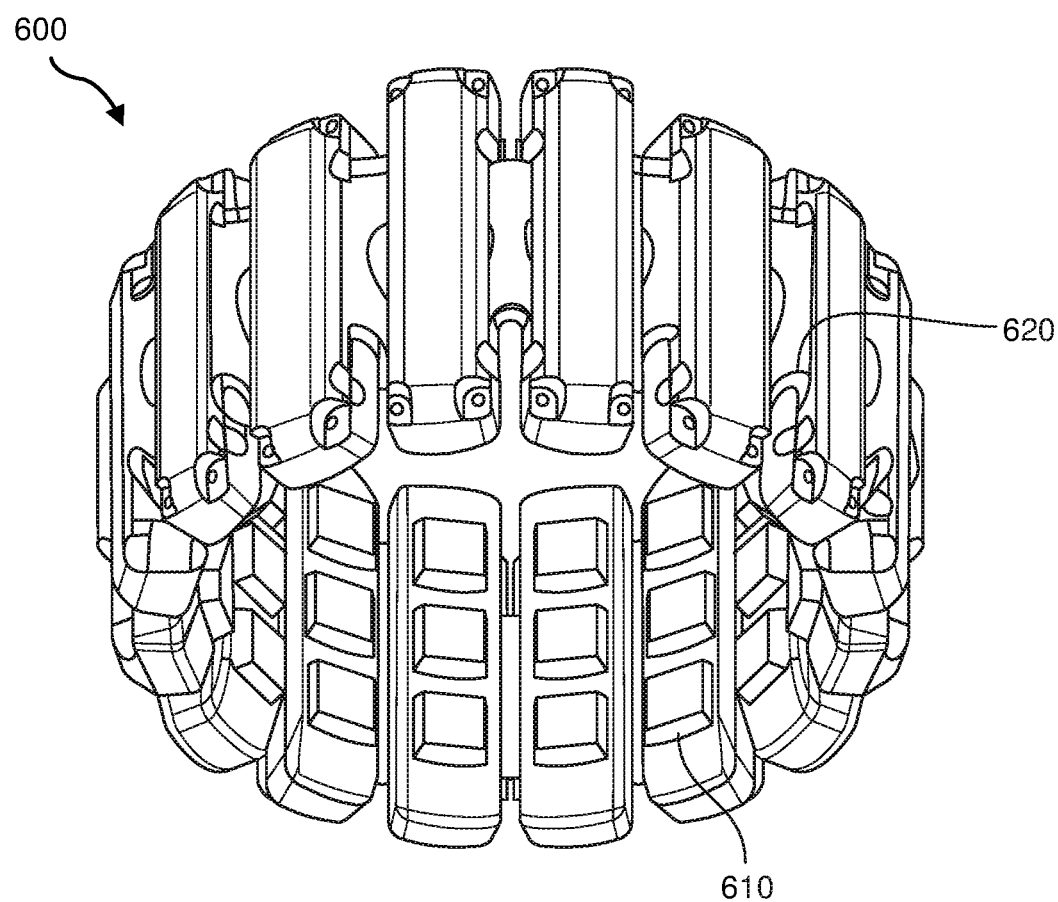
FIG. 6A illustrates a wearable system with EMG sensors arranged circumferentially around an elastic band configured to be worn around a user's lower arm or wrist.
Figure 6B:
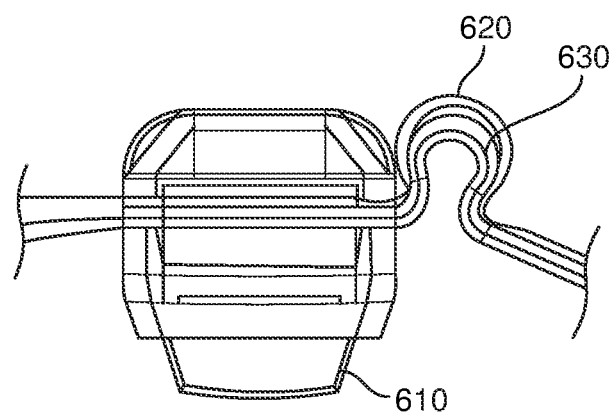
FIG. 6B is a cross-sectional view through one of the EMG sensors illustrated in FIG. 6A.

FIG. 6A below illustrates a man-machine interface (also referred to herein as an EMG control interface) as a wearable system 600 with forty-eight neuromuscular sensors 610 (e.g., EMG sensors) arranged circumferentially around an elastic band 620 configured to be worn around a user's lower arm or wrist. As shown, EMG sensors 610 are arranged circumferentially around elastic band 620. It should be appreciated that any suitable number of neuromuscular sensors may be used. The number and arrangement of neuromuscular sensors may depend on the particular application for which the wearable device is used. For example, a wearable armband or wristband can be used to generate control information for controlling an augmented reality system, a robot, controlling a vehicle, scrolling through text, controlling a virtual avatar, or any other suitable control task. As shown, the sensors may be coupled together using flexible electronics incorporated into the wireless device, FIG. 6B illustrates a cross-sectional view through one of the sensors of the wearable device shown in FIG. 6A.

In some embodiments, the output of one or more of the sensing components can be optionally processed using hardware signal processing circuitry (e.g., to perform amplification, filtering, and/or rectification). In other embodiments, at least some signal processing of the output of the sensing components can be performed in software. Thus, signal processing of signals sampled by the sensors can be performed in hardware, software, or by any suitable combination of hardware and software, as aspects of the technology described herein are not limited in this respect. A non-limiting example of a signal processing chain used to process recorded data from sensors 610 are discussed in more detail below with reference to FIGS. 7A and 7B.

Figure 7A:
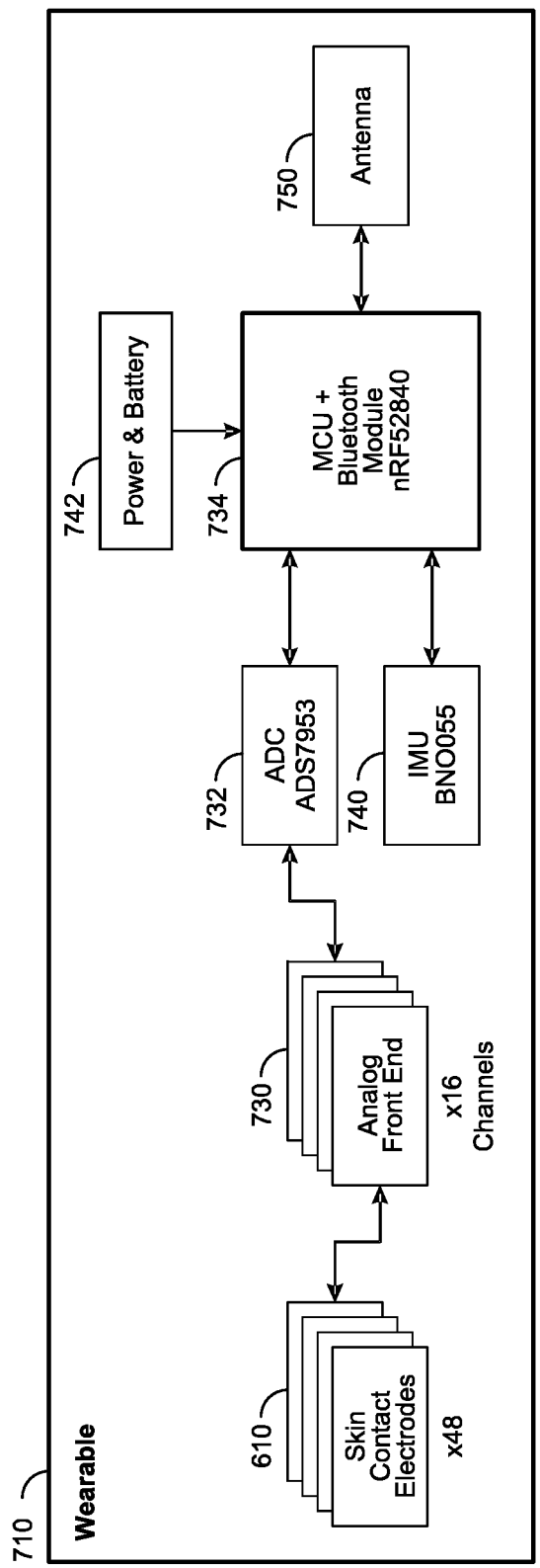
FIGS. 7A and 7B schematically illustrate components of a computer-based system on which some embodiments of the technology described herein are implemented.
Figure 7B:
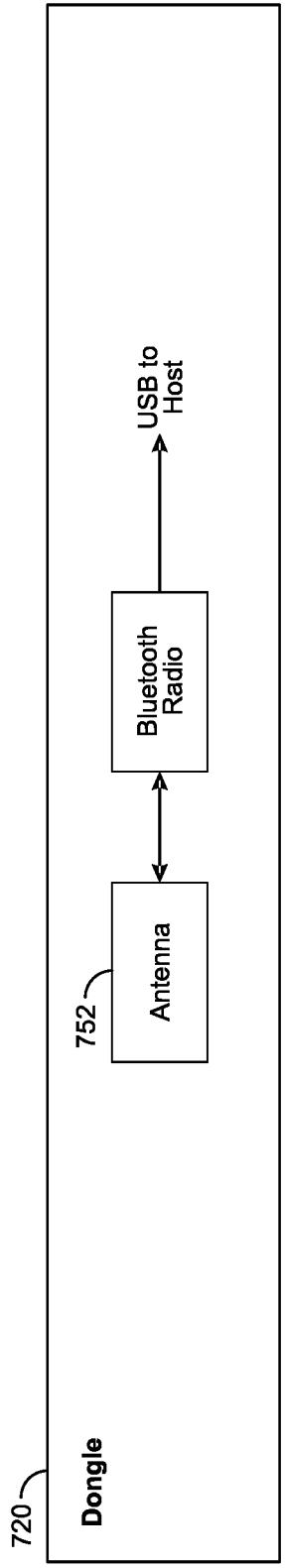

FIGS. 7A and 7B illustrate a schematic diagram with internal components of a wearable system with forty-eight EMG sensors. As shown, the wearable system includes a wearable portion 710 (FIG. 7A) and a dongle portion 720 (FIG. 7B) in communication with the wearable portion 710 (e.g., via Bluetooth or another suitable wireless communication technology). As shown in FIG. 7A, the wearable portion 710 includes sensors 610, examples of which are described in connection with FIGS. 6A and 6B. The output of the sensors 610 is provided to analog front end 730 configured to perform analog processing (e.g., amplification, noise reduction, filtering, etc.) on the recorded signals. The processed analog signals are then provided to analog-to-digital converter 732, which converts the analog signals to digital signals that can be processed by one or more computer processors. An example of a computer processor that may be used in accordance with some embodiments is microcontroller (MCU) 734 illustrated in FIG. 7A. As shown, MCU 734 may also include inputs from other sensors (e.g., IMU sensor 740), and power and battery module 742. The output of the processing performed by MCU may be provided to antenna 750 for transmission to dongle portion 720 shown in FIG. 7B.

Dongle portion 720 includes antenna 752 configured to communicate with antenna 750 included as part of wearable portion 710. Communication between antenna 750 and 752 may occur using any suitable wireless technology and protocol, non-limiting examples of which include radiofrequency signaling and Bluetooth. As shown, the signals received by antenna 752 of dongle portion 720 may be provided to a host computer for further processing, display, and/or for effecting control of a physical or virtual object or objects.

Although the examples provided with reference to FIGS. 6A-6B and FIGS. 7A-7B are discussed in the context of interfaces with EMG sensors, the techniques described herein for reducing electromagnetic interference can also be implemented in wearable interfaces with other types of sensors including, but not limited to, mechanomyography (MMG) sensors, sonomyography (SMG) sensors, and electrical impedance tomography (EIT) sensors. It should also be understood that the techniques described herein for improving neuromuscular sensor data can also be implemented in wearable interfaces that communicate with computer hosts through wires and cables (e.g., USB cables, optical fiber cables).

Figure 8:
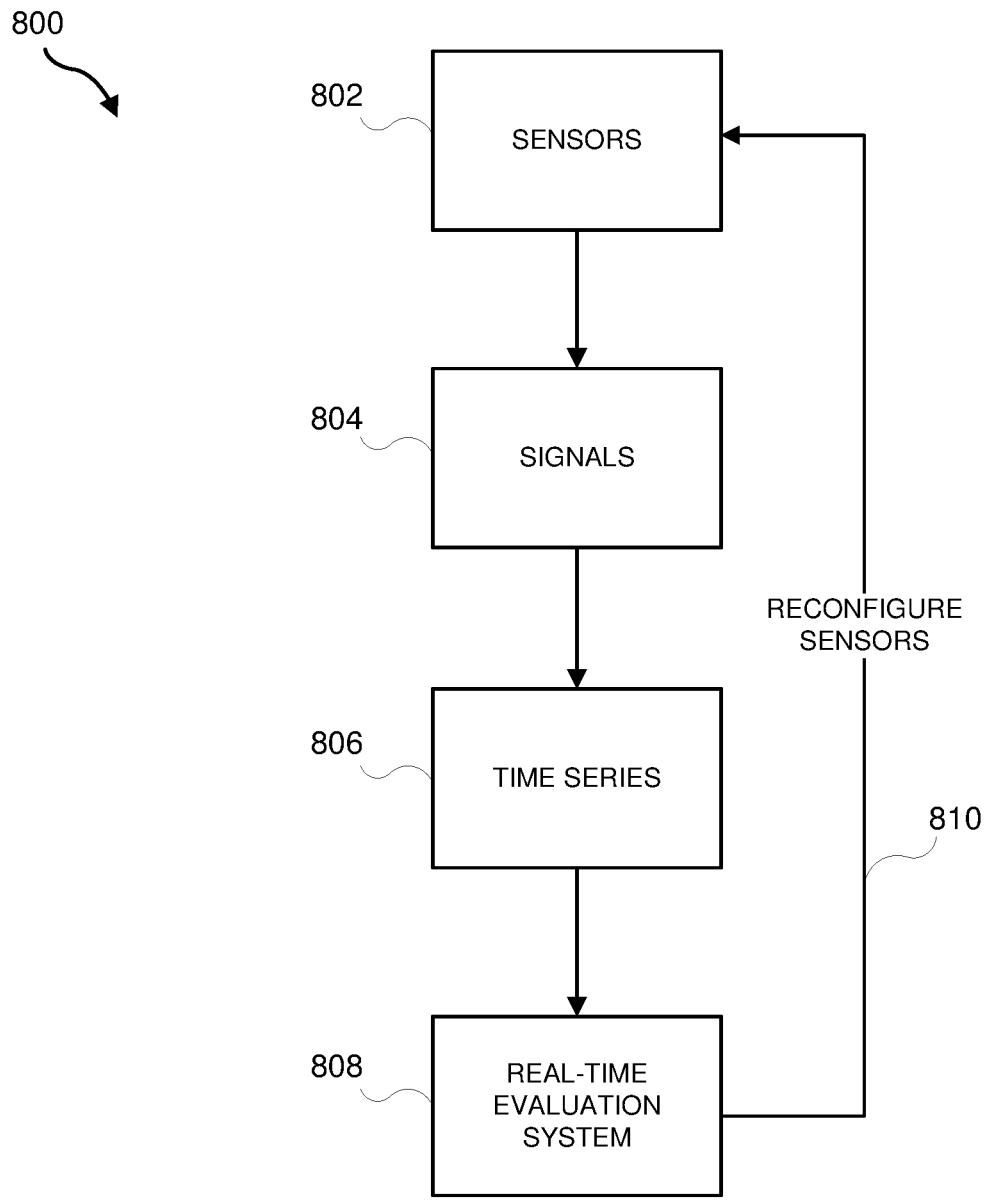
FIG. 8 is a diagram of a computer-based system for configuring neuromuscular sensors based on neuromuscular sensor data.

FIG. 8 shows a computer-based system 800 for configuring neuromuscular sensors based on neuromuscular sensor data in accordance with some embodiments. The system includes a plurality of sensors 802 configured to record signals resulting from the movement of portions of a human body. Sensors 802 may include autonomous sensors.

System 800 also includes one or more computer processors (not shown in FIG. 8) programmed to communicate with sensors 802. For example, signals 804 recorded by one or more of the sensors 802 may be provided to the processor(s), which may be programmed to identify a time series with values acquired via sensors 802. The processor(s), as a part of a real-time system, may evaluate the quality of signals 804 received from, e.g., a single sensor or a pair of differential sensors.

The term "differential sensors," as used herein, may refer to any pair or set of sensors whose signals are compared and/or combined (e.g., by subtracting one from another) to produce a composite signal (e.g., with the end of reducing or eliminating noise from the signals). For example, in the case of electrodes used as neuromuscular sensors, the raw voltage signal from an electrode in the absence of relevant neuromuscular activity may typically represent noise (e.g., ambient electromagnetic noise from the environment). On the assumption that two electrodes will experience the same noise, by subtracting the signal of an electrode only observing noise from the signal of an electrode whose signal represents relevant activity plus noise, the relevant signal may be isolated. However, as described herein, in some cases sensors may experience noise unevenly, and systems and methods described herein may dynamically configure differential sensor pairings to improve the resultant signal.

As discussed above, a real-time system may evaluate, based on received time series data, the performance of a sensor and/or a pair of differential sensors. For example, the real-time system can determine if a particular electrode in a pair of differential electrodes is not in contact with the user's skin. An electrode that is not in contact with the user's skin can generate signals characterized by out-of-range amplitude and frequency discontinuities. The real-time system can reconfigure the array of electrodes to replace or deactivate the channel of the electrode that is not in contact with the user's skin with another electrode determined to be in contact with the user's skin. Thus, the dynamically configurable arrangement of electrodes ensures that only electrodes in contact with the user skin are used to compute measurements.

In some instances, the real-time system configures multiple pairs of sensors in the arrangement, each pair of sensors being used to compute differential measurements. Sensors in each pair do not need to be located at equal distances. Differently stated, sensors in a first pair of sensors can be separated by a first distance, while sensors in a second pair of electrodes can be separated by a second distance, wherein the first distance is different from the second distance. Configuring pairs of sensors, where the sensors in one pair are separated by a different distance than the sensors in another pair results in a flexible and adaptable system capable of retrieving differential measurements from pairs of sensors known to be better predictors of, for example, an amount of applied force, gestures, and/or poses (collectively "interactions") performed by a user. Moreover, this flexible configuration enables the acquisition of differential measurements from electrodes paired according to the direction of a signal propagation (e.g., in a line down the arm or wrist), horizontally across the arm or wrist, or diagonally (both down and horizontally across the arm or wrist). Accordingly, the armband system can be configured to reduce and/or correct motion artifacts by selecting specific electrodes identified as motion resilient when the real-time system detects the infiltration of motion artifacts in the acquired signals.

In some implementations, the real-time system can activate sensors positioned at specific areas of the arm or wrist depending on an activity being performed by the user. For example, when the user engages in a typing task, the real-time system can determine such activity and accordingly can steer the sampling density to the underside arm nerves by, for example, activating and pairing sensors located in such region. For another example, the sampling density can focus on regions of the arm associated with the movement of a finger (e.g., for mission critical discrete controls) or configured in a distributed full arm or wrist sampling configuration when predictions are made regarding the user's handstate.

In some implementations, the configurable array of sensors can reduce the number of channels in the armband system that remain active at a given time. For example, the real-time system can determine that, for a specific task, predictions of interactions performed by a user can be computed from signals received from a first set of sensors, while the signals received from a second set of sensors are discarded or ignored. In such a case, the real-time system can activate the first set of sensors and deactivate the second set of sensors resulting in a more efficient use of computational resources.

In some examples, the systems and methods described herein may dynamically configure sensors in a way that is personalized to the particular user. For example, the shape of the user's arm or wrist, the fit of the wearable device on the user, the characteristics of the neuromuscular signals received from the user, surface qualities of the user's skin, and/or the hairiness of the user's arm may impact how suited various sensors are to producing accurate and/or useful signals (e.g., for a system that converts neuromuscular signals into musculoskeletal representations). In some examples, systems described herein may observe and evaluate sensor performance and quality during specific user-performed tasks. By determining that certain sensors provide more reliable performance during certain tasks for a given user, the systems and methods described herein may dynamically adjust the configurable array of sensors to use data from pairs of differential sensors that provide signals most representative of the user's activity for those tasks. Thus, for example, an XR system that consumes the neuromuscular signals to produce musculoskeletal representations of the user's hand may provide high-level information about activities that the user is engaged in (e.g., typing, interacting with particular types of virtual objects, etc.) or predicted to be engaging in so that systems described herein may adjust the configurable array of sensors according to a stored user profile.

In some examples, systems described herein may prospectively adjust the configurable array of sensors (e.g., based on information received about an application that the user has initiated, an input mode that the user has selected, a task that the user is predicted to start performing). Additionally or alternatively, systems described herein may adjust the configurable array of sensors in response to observed performance issues and/or errors (e.g., detecting that an electrode has come out of contact with the user's skin). In some examples, systems described herein may evaluate sensor performance before providing sensor data to subsystems that consume the sensor data (e.g., an inferential model that produces a musculoskeletal representation of the user's hand based on the neuromuscular sensor data). Additionally or alternatively, systems described herein may partly evaluate sensor performance based on performance issues observed by the subsystems that consume the sensor data. For example, an inferential model (and/or associated subsystems for interpreting neuromuscular data) may produce a musculoskeletal representation with a large expected error term. While systems described herein may attribute some of the error to the inferential model, in some embodiments systems described herein may attribute some of the error to sensor performance. These systems may therefore backpropagate the error to the sensor array, and a real-time system may reconfigure the sensor array at least partly in response to the backpropagated error.

Figure 9:
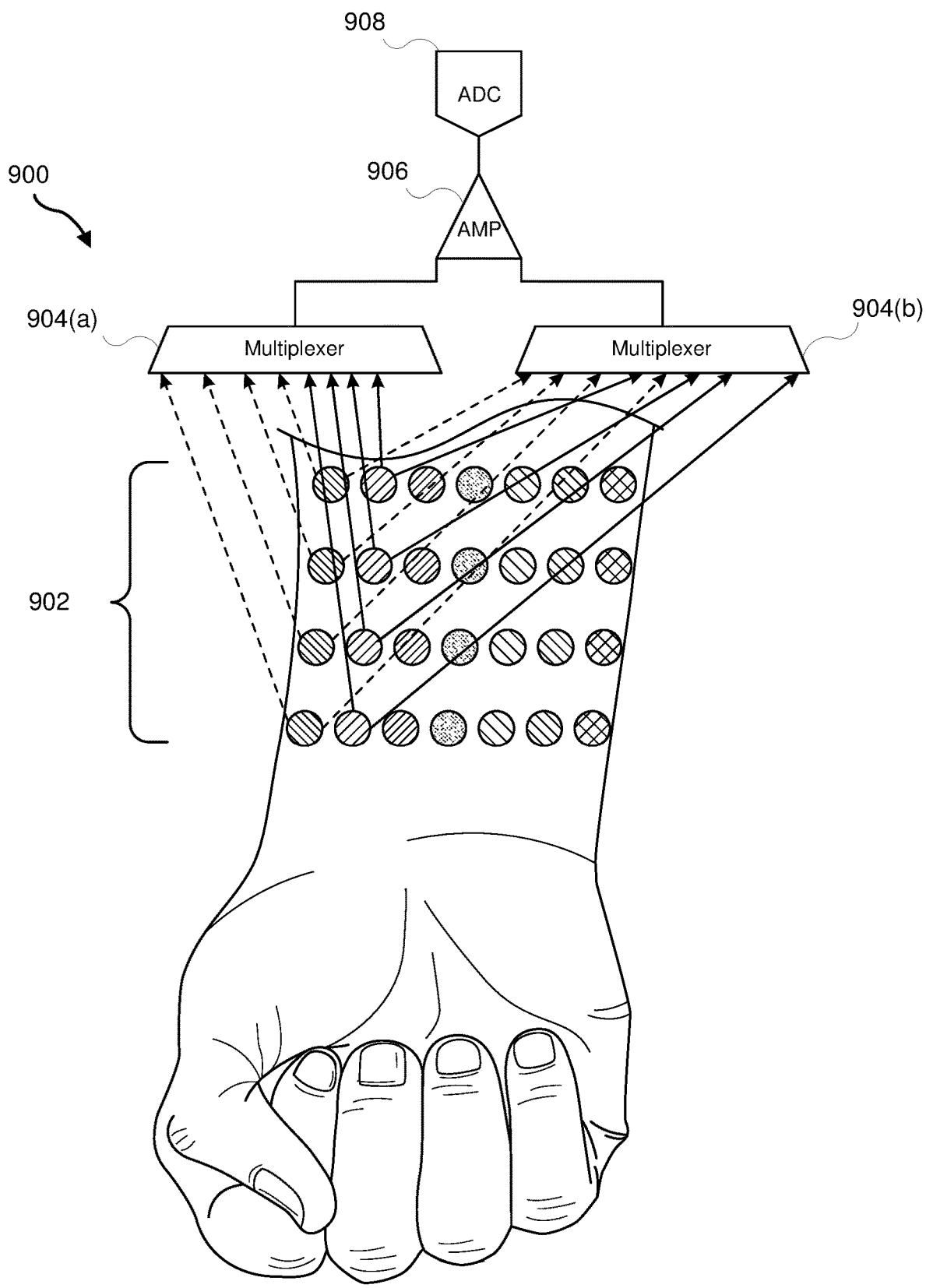
FIG. 9 is an illustration of a dynamically configurable array of neuromuscular sensors.

FIG. 9 shows an example of a system 900 for a dynamically configurable array 902 of electrodes. The dynamically configurable array can be integrated in the armband system shown in FIGS. 6A-6B and FIGS. 7A-7B. Electrodes in an array, as shown in FIG. 9, can be wired to a fully switched/multiplexed matrix in a configuration that enables any electrode in the array to be paired with any other electrode in the same array. Thus, signals from dynamically configurable array 902 may be received by multiplexers 904(a)-(b), which may pass the resultant signal to an amplifier 906. Amplifier 906 may, in turn, pass the signal to an analog-to-digital converter 908.

Figure 10:
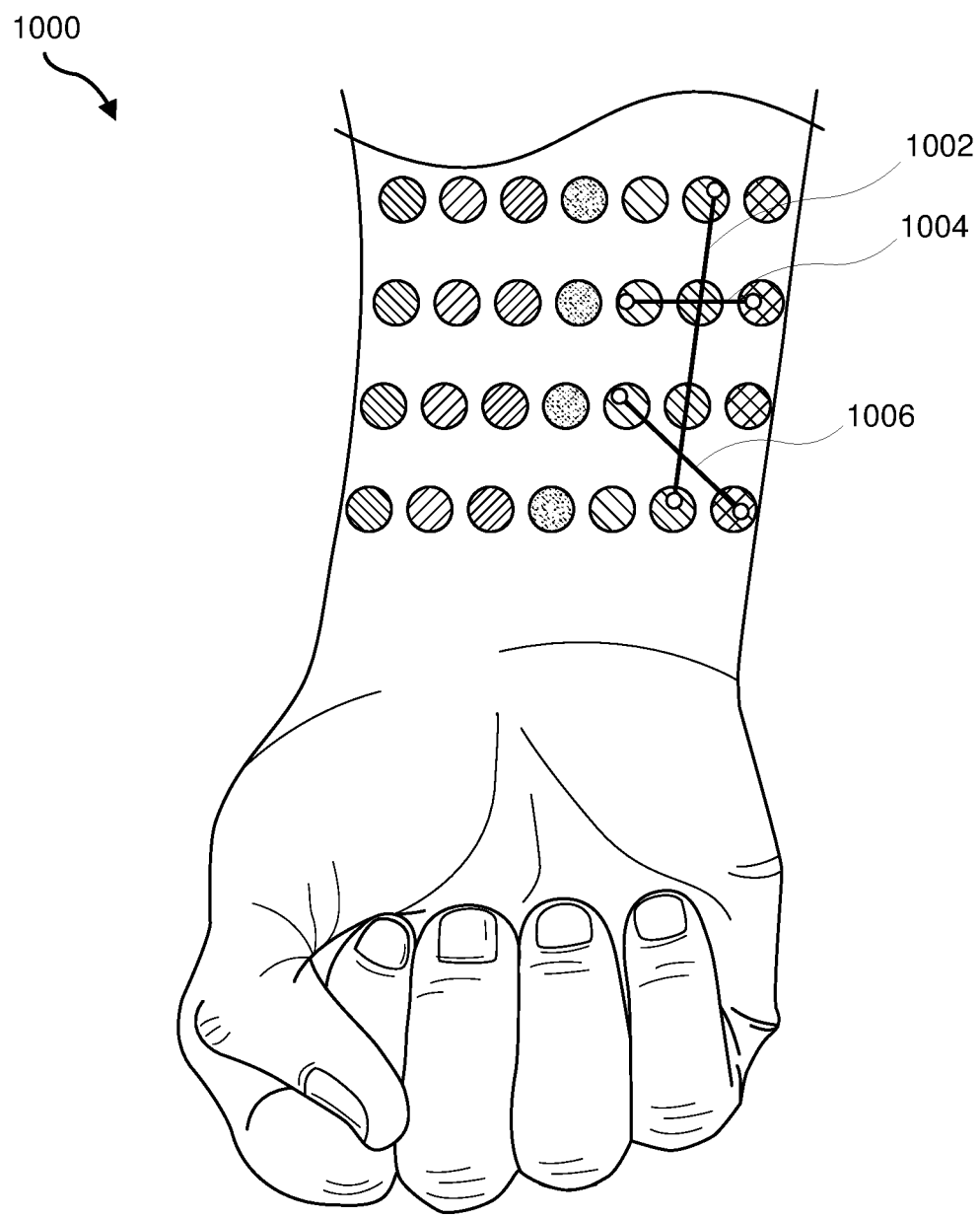
FIG. 10 is an illustration of potential differential pairings of neuromuscular sensors.

FIG. 10 shows example differential sensor pairings within the dynamically configurable array 902 of electrodes shown in FIG. 9. As shown in FIG. 10, sensors that run longitudinally along the user's wrist may be paired, as illustrated by example pairing 1002. In another example, sensors that run horizontally across the user's wrist may be paired, as illustrated by pairing 1004. Furthermore, sensors that are positioned diagonally from each other (e.g., not positioned strictly longitudinally or horizontally from each other) may be paired, as illustrated by pairing 1006. In addition, it may be appreciated that the various example sensor pairings may involve differing sensor distances.

Figure 11:
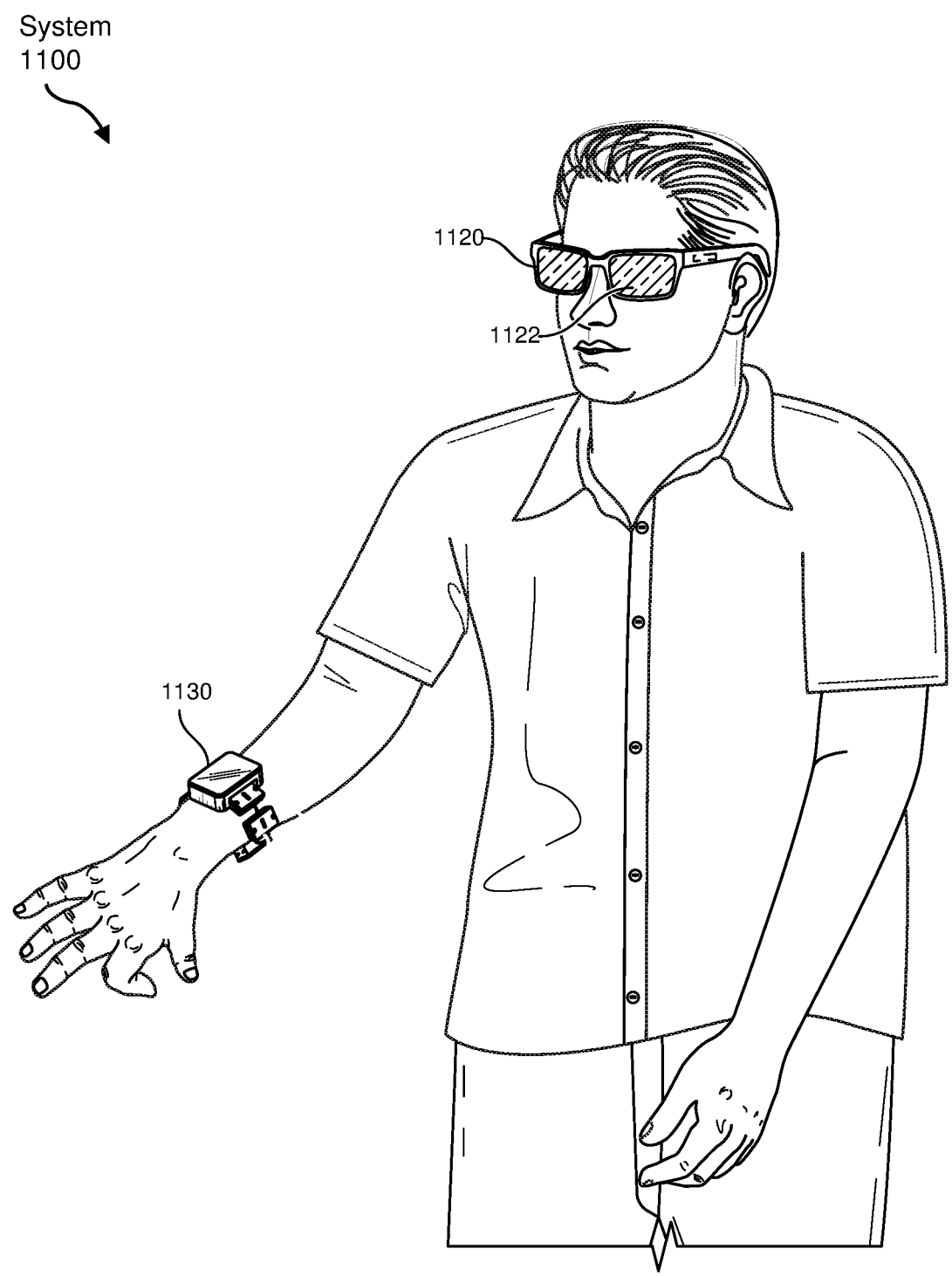
FIG. 11 illustrates an extended reality (XR) system including a headset configured to be worn on a user's head and a wearable control device configured to be worn on the user's arm or wrist, in accordance with some embodiments of the technology described herein.

In some embodiments, the wearable device may be used in association with a virtual reality (VR), augmented reality (AR) and/or extended reality (XR) systems. In one example system shown in FIG. 11, the XR system 1100 comprises a headset 1120 (e.g., augmented reality glasses with one or more displays 1122) configured to be worn on a user's head, and a wearable control device configured to be worn on the user's arm or wrist. The wearable control device 1130 comprises analog signal chain circuitry comprising at least one amplifier configured to amplify analog electrical signals recorded from a body of the user, and an analog-to-digital converter configured to convert the amplified analog electrical signals to digital signals which can be used to control the virtual reality (VR), augmented reality (AR) and/or extended reality (XR) systems.

EXAMPLE EMBODIMENTS

Example 1

A computer-implemented method for detecting and compensating for motion artifacts in a multiple electrode wearable system may include (i) receiving a set of neuromuscular signals from a plurality of neuromuscular sensors within the arrangement of neuromuscular sensors, (ii) determining, via a real-time system, at least one sensor error included in a neuromuscular signal from the set of neuromuscular signals, wherein the neuromuscular signal is associated with a first neuromuscular sensor included in the plurality of neuromuscular sensors, and (iii) reconfiguring, in response to determining the at least one sensor error, the arrangement of neuromuscular sensors to replace use of the first neuromuscular sensor from the plurality of neuromuscular sensors with use of a second neuromuscular sensor from the arrangement of neuromuscular sensors.

Example 2

The computer-implemented method of Example 1, where replacing use of the first neuromuscular sensor with use of the second neuromuscular sensor comprises replacing use of a first differential pair of neuromuscular sensors that comprises the first neuromuscular sensor with use of a second differential pair of neuromuscular sensors that comprises the second neuromuscular sensor.

Example 3

The computer-implemented method of Example 1, where determining the at least one sensor error comprises detecting a loss of contact between the first neuromuscular sensor and the user's skin.

Example 4

The computer-implemented method of Example 3, where detecting the loss of contact comprises at least one of (i) determining that the neuromuscular signal comprises an amplitude outside a predetermined range, or (ii) determining that the neuromuscular signal comprises a frequency discontinuity.

Example 5

The computer-implemented method of Example 1, where the reconfigured arrangement of neuromuscular sensors includes (i) a first differential pair of neuromuscular sensors separated by a first distance, and (ii) a second differential pair of neuromuscular sensors separated by a second distance, wherein the first distance differs from the second distance.

Example 6

The computer-implemented method of Example 1, the reconfigured arrangement of neuromuscular sensors includes (i) a first differential pair of neuromuscular sensors along a first line, and (ii) a second differential pair of neuromuscular sensors along a second line, wherein the first line and the second line are not substantially parallel.

Example 7

The computer-implemented method of Example 1, further including identifying an interaction being performed by the user, wherein determining the sensor error comprises determining that use of the first neuromuscular sensor yields the sensor error during the interaction.

Example 8

The computer-implemented method of Example 1, where (i) receiving the set of neuromuscular signals comprises receiving the set of neuromuscular signals during a first session, and (ii) determining the sensor error comprises prospectively determining the sensor error during a second session based on the set of neuromuscular signals received during the first session.

Example 9

The computer-implemented method of Example 1, where reconfiguring the arrangement of neuromuscular sensors is based at least in part on a user profile of the user.

Example 10

The computer-implemented method of Example 1, where reconfiguring the arrangement of neuromuscular sensors comprises deactivating a channel of neuromuscular sensors within the arrangement of neuromuscular sensors.

Figure 12:
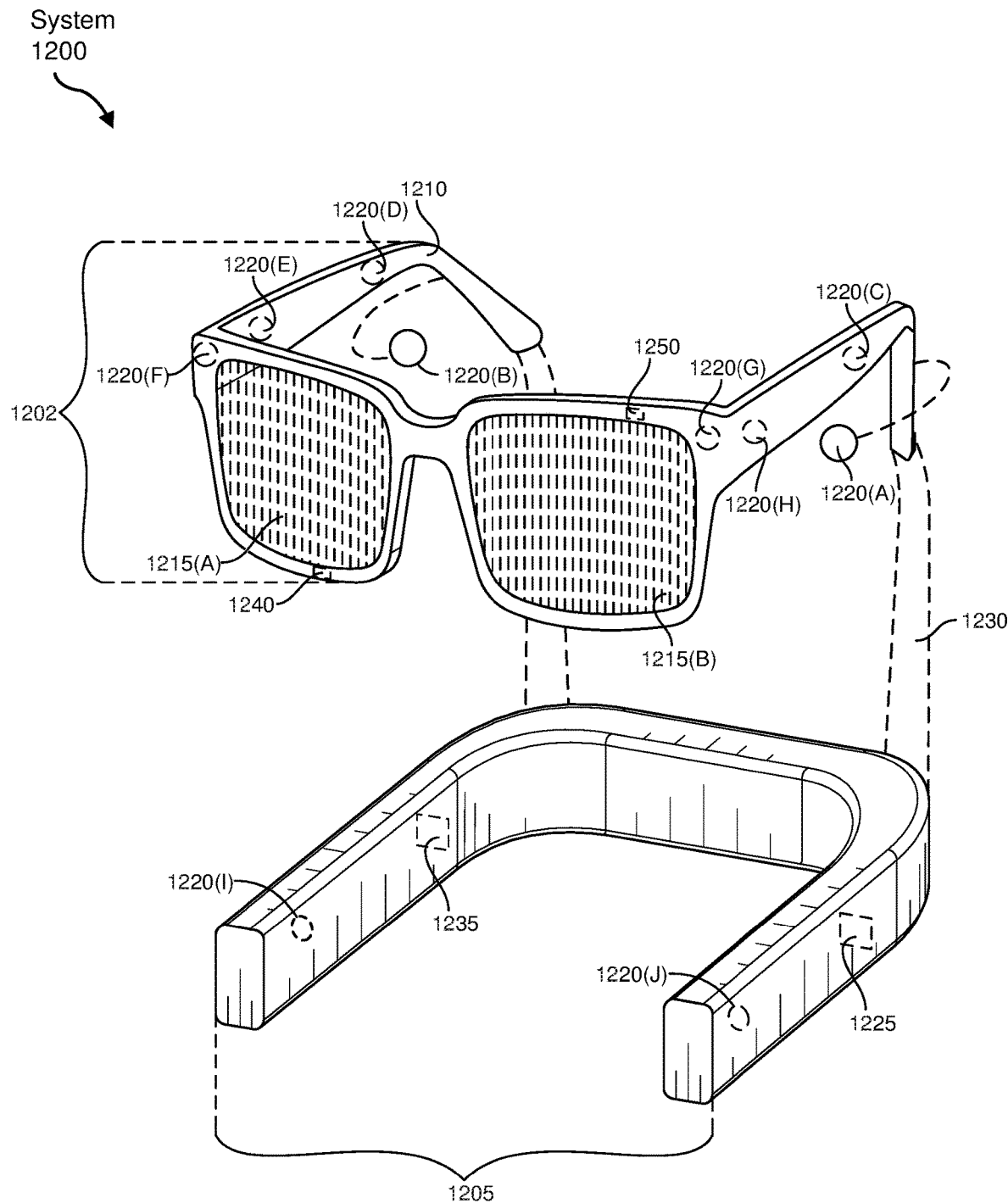
FIG. 12 is an illustration of exemplary augmented-reality glasses that may be used in connection with embodiments of this disclosure.

Turning to FIG. 12, augmented-reality system 1200 may include an eyewear device 1202 with a frame 1210 configured to hold a left display device 1215(A) and a right display device 1215(B) in front of a user's eyes. Display devices 1215(A) and 1215(B) may act together or independently to present an image or series of images to a user. While augmented-reality system 1200 includes two displays, embodiments of this disclosure may be implemented in augmented-reality systems with a single NED or more than two NEDs.

In some embodiments, augmented-reality system 1200 may include one or more sensors, such as sensor 1240. Sensor 1240 may generate measurement signals in response to motion of augmented-reality system 1200 and may be located on substantially any portion of frame 1210. Sensor 1240 may represent one or more of a variety of different sensing mechanisms, such as a position sensor, an inertial measurement unit (IMU), a depth camera assembly, a structured light emitter and/or detector, or any combination thereof. In some embodiments, augmented-reality system 1200 may or may not include sensor 1240 or may include more than one sensor. In embodiments in which sensor 1240 includes an IMU, the IMU may generate calibration data based on measurement signals from sensor 1240. Examples of sensor 1240 may include, without limitation, accelerometers, gyroscopes, magnetometers, other suitable types of sensors that detect motion, sensors used for error correction of the IMU, or some combination thereof.

Figure 13:
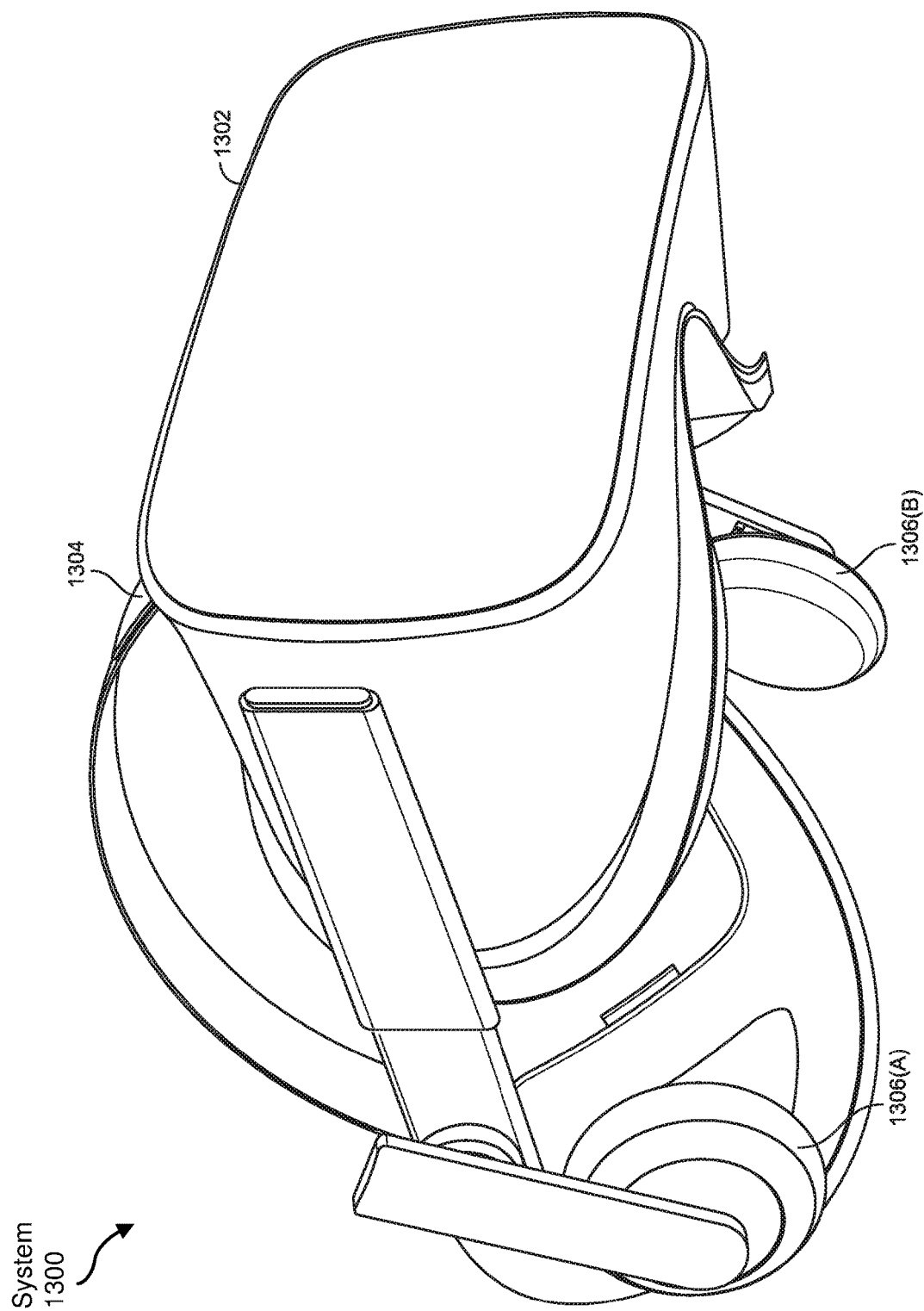
FIG. 13 is an illustration of an exemplary virtual-reality headset that may be used in connection with embodiments of this disclosure.

In some examples, augmented-reality system 1200 may also include a microphone array with a plurality of acoustic transducers 1220(A)-1220(J), referred to collectively as acoustic transducers 1220. Acoustic transducers 1220 may represent transducers that detect air pressure variations induced by sound waves. Each acoustic transducer 1220 may be configured to detect sound and convert the detected sound into an electronic format (e.g., an analog or digital format). The microphone array in FIG. 13 may include, for example, ten acoustic transducers: 1220(A) and 1220(B), which may be designed to be placed inside a corresponding ear of the user, acoustic transducers 1220(C), 1220(D), 1220(E), 1220(F), 1220(G), and 1220(H), which may be positioned at various locations on frame 1210, and/or acoustic transducers 1220(1) and 1220(J), which may be positioned on a corresponding neckband 1205.

In some embodiments, one or more of acoustic transducers 1220(A)-(F) may be used as output transducers (e.g., speakers). For example, acoustic transducers 1220(A) and/or 1220(B) may be earbuds or any other suitable type of headphone or speaker.

The configuration of acoustic transducers 1220 of the microphone array may vary. While augmented-reality system 1200 is shown in FIG. 12 as having ten acoustic transducers 1220, the number of acoustic transducers 1220 may be greater or less than ten. In some embodiments, using higher numbers of acoustic transducers 1220 may increase the amount of audio information collected and/or the sensitivity and accuracy of the audio information. In contrast, using a lower number of acoustic transducers 1220 may decrease the computing power required by an associated controller 1250 to process the collected audio information. In addition, the position of each acoustic transducer 1220 of the microphone array may vary. For example, the position of an acoustic transducer 1220 may include a defined position on the user, a defined coordinate on frame 1210, an orientation associated with each acoustic transducer 1220, or some combination thereof.

Acoustic transducers 1220(A) and 1220(B) may be positioned on different parts of the user's ear, such as behind the pinna, behind the tragus, and/or within the auricle or fossa. Or, there may be additional acoustic transducers 1220 on or surrounding the ear in addition to acoustic transducers 1220 inside the ear canal. Having an acoustic transducer 1220 positioned next to an ear canal of a user may enable the microphone array to collect information on how sounds arrive at the ear canal. By positioning at least two of acoustic transducers 1220 on either side of a user's head (e.g., as binaural microphones), augmented-reality device 1200 may simulate binaural hearing and capture a 3D stereo sound field around about a user's head. In some embodiments, acoustic transducers 1220(A) and 1220(B) may be connected to augmented-reality system 1200 via a wired connection 1230, and in other embodiments acoustic transducers 1220(A) and 1220(B) may be connected to augmented-reality system 1200 via a wireless connection (e.g., a Bluetooth connection). In still other embodiments, acoustic transducers 1220(A) and 1220(B) may not be used at all in conjunction with augmented-reality system 1200.

Acoustic transducers 1220 on frame 1210 may be positioned in a variety of different ways, including along the length of the temples, across the bridge, above or below display devices 1215(A) and 1215(B), or some combination thereof. Acoustic transducers 1220 may also be oriented such that the microphone array is able to detect sounds in a wide range of directions surrounding the user wearing the augmented-reality system 1200. In some embodiments, an optimization process may be performed during manufacturing of augmented-reality system 1200 to determine relative positioning of each acoustic transducer 1220 in the microphone array.

In some examples, augmented-reality system 1200 may include or be connected to an external device (e.g., a paired device), such as neckband 1205. Neckband 1205 generally represents any type or form of paired device. Thus, the following discussion of neckband 1205 may also apply to various other paired devices, such as charging cases, smart watches, smart phones, wrist bands, other wearable devices, hand-held controllers, tablet computers, laptop computers, other external compute devices, etc.

As shown, neckband 1205 may be coupled to eyewear device 1202 via one or more connectors. The connectors may be wired or wireless and may include electrical and/or non-electrical (e.g., structural) components. In some cases, eyewear device 1202 and neckband 1205 may operate independently without any wired or wireless connection between them. While FIG. 12 illustrates the components of eyewear device 1202 and neckband 1205 in example locations on eyewear device 1202 and neckband 1205, the components may be located elsewhere and/or distributed differently on eyewear device 1202 and/or neckband 1205. In some embodiments, the components of eyewear device 1202 and neckband 1205 may be located on one or more additional peripheral devices paired with eyewear device 1202, neckband 1205, or some combination thereof.

Pairing external devices, such as neckband 1205, with augmented-reality eyewear devices may enable the eyewear devices to achieve the form factor of a pair of glasses while still providing sufficient battery and computation power for expanded capabilities. Some or all of the battery power, computational resources, and/or additional features of augmented-reality system 1200 may be provided by a paired device or shared between a paired device and an eyewear device, thus reducing the weight, heat profile, and form factor of the eyewear device overall while still retaining desired functionality. For example, neckband 1205 may allow components that would otherwise be included on an eyewear device to be included in neckband 1205 since users may tolerate a heavier weight load on their shoulders than they would tolerate on their heads. Neckband 1205 may also have a larger surface area over which to diffuse and disperse heat to the ambient environment. Thus, neckband 1205 may allow for greater battery and computation capacity than might otherwise have been possible on a stand-alone eyewear device. Since weight carried in neckband 1205 may be less invasive to a user than weight carried in eyewear device 1202, a user may tolerate wearing a lighter eyewear device and carrying or wearing the paired device for greater lengths of time than a user would tolerate wearing a heavy stand-alone eyewear device, thereby enabling users to more fully incorporate artificial-reality environments into their day-to-day activities.

Neckband 1205 may be communicatively coupled with eyewear device 1202 and/or to other devices. These other devices may provide certain functions (e.g., tracking, localizing, depth mapping, processing, storage, etc.) to augmented-reality system 1200. In the embodiment of FIG. 12, neckband 1205 may include two acoustic transducers (e.g., 1220(1) and 1220(J)) that are part of the microphone array (or potentially form their own microphone subarray). Neckband 1205 may also include a controller 1225 and a power source 1235.

Acoustic transducers 1220(1) and 1220(J) of neckband 1205 may be configured to detect sound and convert the detected sound into an electronic format (analog or digital). In the embodiment of FIG. 12, acoustic transducers 1220(1) and 1220(J) may be positioned on neckband 1205, thereby increasing the distance between the neckband acoustic transducers 1220(1) and 1220(J) and other acoustic transducers 1220 positioned on eyewear device 1202. In some cases, increasing the distance between acoustic transducers 1220 of the microphone array may improve the accuracy of beamforming performed via the microphone array. For example, if a sound is detected by acoustic transducers 1220(C) and 1220(D) and the distance between acoustic transducers 1220(C) and 1220(D) is greater than, e.g., the distance between acoustic transducers 1220(D) and 1220(E), the determined source location of the detected sound may be more accurate than if the sound had been detected by acoustic transducers 1220(D) and 1220(E).

Controller 1225 of neckband 1205 may process information generated by the sensors on neckband 1205 and/or augmented-reality system 1200. For example, controller 1225 may process information from the microphone array that describes sounds detected by the microphone array. For each detected sound, controller 1225 may perform a direction-of-arrival (DOA) estimation to estimate a direction from which the detected sound arrived at the microphone array. As the microphone array detects sounds, controller 1225 may populate an audio data set with the information. In embodiments in which augmented-reality system 1200 includes an inertial measurement unit, controller 1225 may compute all inertial and spatial calculations from the IMU located on eyewear device 1202. A connector may convey information between augmented-reality system 1200 and neckband 1205 and between augmented-reality system 1200 and controller 1225. The information may be in the form of optical data, electrical data, wireless data, or any other transmittable data form. Moving the processing of information generated by augmented-reality system 1200 to neckband 1205 may reduce weight and heat in eyewear device 1202, making it more comfortable to the user.

Power source 1235 in neckband 1205 may provide power to eyewear device 1202 and/or to neckband 1205. Power source 1235 may include, without limitation, lithium ion batteries, lithium-polymer batteries, primary lithium batteries, alkaline batteries, or any other form of power storage. In some cases, power source 1235 may be a wired power source. Including power source 1235 on neckband 1205 instead of on eyewear device 1202 may help better distribute the weight and heat generated by power source 1235.

As noted, some artificial-reality systems may, instead of blending an artificial reality with actual reality, substantially replace one or more of a user's sensory perceptions of the real world with a virtual experience. One example of this type of system is a head-worn display system, such as virtual-reality system 1300 in FIG. 13, that mostly or completely covers a user's field of view. Virtual-reality system 1300 may include a front rigid body 1302 and a band 1304 shaped to fit around a user's head. Virtual-reality system 1300 may also include output audio transducers 1306(A) and 1306(B). Furthermore, while not shown in FIG. 13, front rigid body 1302 may include one or more electronic elements, including one or more electronic displays, one or more inertial measurement units (IMUS), one or more tracking emitters or detectors, and/or any other suitable device or system for creating an artificial-reality experience.

Artificial-reality systems may include a variety of types of visual feedback mechanisms. For example, display devices in augmented-reality system 1200 and/or virtual-reality system 1300 may include one or more liquid crystal displays (LCDs), light emitting diode (LED) displays, organic LED (OLED) displays, digital light project (DLP) micro-displays, liquid crystal on silicon (LCoS) micro-displays, and/or any other suitable type of display screen. These artificial-reality systems may include a single display screen for both eyes or may provide a display screen for each eye, which may allow for additional flexibility for varifocal adjustments or for correcting a user's refractive error. Some of these artificial-reality systems may also include optical subsystems having one or more lenses (e.g., conventional concave or convex lenses, Fresnel lenses, adjustable liquid lenses, etc.) through which a user may view a display screen. These optical subsystems may serve a variety of purposes, including to collimate (e.g., make an object appear at a greater distance than its physical distance), to magnify (e.g., make an object appear larger than its actual size), and/or to relay (to, e.g., the viewer's eyes) light. These optical subsystems may be used in a non-pupil-forming architecture (such as a single lens configuration that directly collimates light but results in so-called pincushion distortion) and/or a pupil-forming architecture (such as a multi-lens configuration that produces so-called barrel distortion to nullify pincushion distortion).

In addition to or instead of using display screens, some the artificial-reality systems described herein may include one or more projection systems. For example, display devices in augmented-reality system 1200 and/or virtual-reality system 1300 may include micro-LED projectors that project light (using, e.g., a waveguide) into display devices, such as clear combiner lenses that allow ambient light to pass through. The display devices may refract the projected light toward a user's pupil and may enable a user to simultaneously view both artificial-reality content and the real world. The display devices may accomplish this using any of a variety of different optical components, including waveguide components (e.g., holographic, planar, diffractive, polarized, and/or reflective waveguide elements), light-manipulation surfaces and elements (such as diffractive, reflective, and refractive elements and gratings), coupling elements, etc. Artificial-reality systems may also be configured with any other suitable type or form of image projection system, such as retinal projectors used in virtual retina displays.

The artificial-reality systems described herein may also include various types of computer vision components and subsystems. For example, augmented-reality system 1200 and/or virtual-reality system 1300 may include one or more optical sensors, such as two-dimensional (2D) or 3D cameras, structured light transmitters and detectors, time-of-flight depth sensors, single-beam or sweeping laser rangefinders, 3D LiDAR sensors, and/or any other suitable type or form of optical sensor. An artificial-reality system may process data from one or more of these sensors to identify a location of a user, to map the real world, to provide a user with context about real-world surroundings, and/or to perform a variety of other functions.

The artificial-reality systems described herein may also include one or more input and/or output audio transducers. Output audio transducers may include voice coil speakers, ribbon speakers, electrostatic speakers, piezoelectric speakers, bone conduction transducers, cartilage conduction transducers, tragus-vibration transducers, and/or any other suitable type or form of audio transducer. Similarly, input audio transducers may include condenser microphones, dynamic microphones, ribbon microphones, and/or any other type or form of input transducer. In some embodiments, a single transducer may be used for both audio input and audio output.

In some embodiments, the artificial-reality systems described herein may also include tactile (i.e., haptic) feedback systems, which may be incorporated into headwear, gloves, body suits, handheld controllers, environmental devices (e.g., chairs, floormats, etc.), and/or any other type of device or system. Haptic feedback systems may provide various types of cutaneous feedback, including vibration, force, traction, texture, and/or temperature. Haptic feedback systems may also provide various types of kinesthetic feedback, such as motion and compliance. Haptic feedback may be implemented using motors, piezoelectric actuators, fluidic systems, and/or a variety of other types of feedback mechanisms. Haptic feedback systems may be implemented independent of other artificial-reality devices, within other artificial-reality devices, and/or in conjunction with other artificial-reality devices.

By providing haptic sensations, audible content, and/or visual content, artificial-reality systems may create an entire virtual experience or enhance a user's real-world experience in a variety of contexts and environments. For instance, artificial-reality systems may assist or extend a user's perception, memory, or cognition within a particular environment. Some systems may enhance a user's interactions with other people in the real world or may enable more immersive interactions with other people in a virtual world. Artificial-reality systems may also be used for educational purposes (e.g., for teaching or training in schools, hospitals, government organizations, military organizations, business enterprises, etc.), entertainment purposes (e.g., for playing video games, listening to music, watching video content, etc.), and/or for accessibility purposes (e.g., as hearing aids, visual aids, etc.). The embodiments disclosed herein may enable or enhance a user's artificial-reality experience in one or more of these contexts and environments and/or in other contexts and environments.

As detailed above, the computing devices and systems described and/or illustrated herein broadly represent any type or form of computing device or system capable of executing computer-readable instructions, such as those contained within the modules described herein. In their most basic configuration, these computing device(s) may each include at least one memory device and at least one physical processor.

In some examples, the term "memory device" generally refers to any type or form of volatile or non-volatile storage device or medium capable of storing data and/or computer-readable instructions. In one example, a memory device may store, load, and/or maintain one or more of the modules described herein. Examples of memory devices include, without limitation, Random Access Memory (RAM), Read Only Memory (ROM), flash memory, Hard Disk Drives (HDDs), Solid-State Drives (SSDs), optical disk drives, caches, variations or combinations of one or more of the same, or any other suitable storage memory.

In some examples, the term "physical processor" (also referred to herein as simply a "processor") generally refers to any type or form of hardware-implemented processing unit capable of interpreting and/or executing computer-readable instructions. In one example, a physical processor may access and/or modify one or more modules stored in the above-described memory device. Examples of physical processors include, without limitation, microprocessors, microcontrollers, Central Processing Units (CPUs), Field-Programmable Gate Arrays (FPGAs) that implement softcore processors, Application-Specific Integrated Circuits (ASICs), portions of one or more of the same, variations or combinations of one or more of the same, or any other suitable physical processor.

Although illustrated as separate elements, the modules described and/or illustrated herein may represent portions of a single module or application. In addition, in certain embodiments one or more of these modules may represent one or more software applications or programs that, when executed by a computing device, may cause the computing device to perform one or more tasks. For example, one or more of the modules described and/or illustrated herein may represent modules stored and configured to run on one or more of the computing devices or systems described and/or illustrated herein. One or more of these modules may also represent all or portions of one or more special-purpose computers configured to perform one or more tasks.

In addition, one or more of the modules described herein may transform data, physical devices, and/or representations of physical devices from one form to another. For example, one or more of the modules recited herein may receive neuromuscular sensor data to be transformed, transform the neuromuscular sensor data, output a result of the transformation to generate a musculoskeletal representation of at least a part of a body, use the result of the transformation to create a visualization of the part of the body in a virtualized environment and/or to provide gesture-based input to a computing device, and store the result of the transformation. Additionally or alternatively, one or more of the modules recited herein may transform a processor, volatile memory, non-volatile memory, and/or any other portion of a physical computing device from one form to another by executing on the computing device, storing data on the computing device, and/or otherwise interacting with the computing device.

In some embodiments, the term "computer-readable medium" generally refers to any form of device, carrier, or medium capable of storing or carrying computer-readable instructions. Examples of computer-readable media include, without limitation, transmission-type media, such as carrier waves, and non-transitory-type media, such as magnetic-storage media (e.g., hard disk drives, tape drives, and floppy disks), optical-storage media (e.g., Compact Disks (CDs), Digital Video Disks (DVDs), and BLU-RAY disks), electronic-storage media (e.g., solid-state drives and flash media), and other distribution systems.

The process parameters and sequence of the steps described and/or illustrated herein are given by way of example only and can be varied as desired. For example, while the steps illustrated and/or described herein may be shown or discussed in a particular order, these steps do not necessarily need to be performed in the order illustrated or discussed. The various exemplary methods described and/or illustrated herein may also omit one or more of the steps described or illustrated herein or include additional steps in addition to those disclosed.

The preceding description has been provided to enable others skilled in the art to best utilize various aspects of the exemplary embodiments disclosed herein. This exemplary description is not intended to be exhaustive or to be limited to any precise form disclosed. Many modifications and variations are possible without departing from the spirit and scope of the present disclosure. The embodiments disclosed herein should be considered in all respects illustrative and not restrictive. Reference should be made to the appended claims and their equivalents in determining the scope of the present disclosure.

Unless otherwise noted, the terms "connected to" and "coupled to" (and their derivatives), as used in the specification and claims, are to be construed as permitting both direct and indirect (i.e., via other elements or components) connection. In addition, the terms "a" or "an," as used in the specification and claims, are to be construed as meaning "at least one of." Finally, for ease of use, the terms "including" and "having" (and their derivatives), as used in the specification and claims, are interchangeable with and have the same meaning as the word "comprising."

What is claimed is:

1. A wearable arm or wrist band system comprising:
a plurality of neuromuscular sensors that detect a plurality of neuromuscular signals from a user;
at least one multiplexer in communication with the plurality of neuromuscular sensors, wherein the multiplexer is capable of dynamically adjusting neuromuscular sensor processing based on neuromuscular signal characteristics;
at least one processor in communication with the plurality of neuromuscular sensors and the at least one multiplexer;
memory comprising computer-executable instructions that, when executed by the processor, cause the processor to:
receive a set of neuromuscular signals from the plurality of neuromuscular sensors;
determine, via a real-time system, at least one signal characteristic for a first neuromuscular signal from the set of neuromuscular signals, wherein the first neuromuscular signal is associated with a first neuromuscular sensor included in the plurality of neuromuscular sensors; and
dynamically reconfigure the processing of neuromuscular signals from the plurality of neuromuscular sensors based on an output from the at least one multiplexer.

2. The system of claim 1, wherein dynamically reconfiguring the processing of neuromuscular signals from the plurality of neuromuscular sensors comprises replacing use of the first neuromuscular sensor with use of a second neuromuscular sensor within the plurality of neuromuscular sensors.

3. The system of claim 1, wherein dynamically reconfiguring the processing of neuromuscular signals from the plurality of neuromuscular sensors comprises adjusting the amount of data being collected from the first neuromuscular sensor by upsampling or downsampling.

4. The system of claim 1, wherein determining the at least one signal characteristic comprises a signal propagation direction associated with the first neuromuscular signal.

5. The system of claim 1, wherein determining the at least one signal characteristic comprises detecting a loss of contact between the first neuromuscular sensor and the user's skin.

6. The system of claim 5, wherein detecting the loss of contact comprises at least one of:
determining that the neuromuscular signal comprises an amplitude outside a predetermined range; or
determining that the neuromuscular signal comprises a frequency discontinuity.

7. The system of claim 1, wherein the plurality of neuromuscular sensors comprises:
a first differential pair of neuromuscular sensors separated by a first distance; and
a second differential pair of neuromuscular sensors separated by a second distance, wherein the first distance differs from the second distance.

8. The system of claim 1, wherein the plurality of neuromuscular sensors comprises:
a first differential pair of neuromuscular sensors being along a first line; and
a second differential pair of neuromuscular sensors being along a second line, wherein the first line and the second line are not substantially parallel.

9. The system of claim 1, wherein the computer-executable instructions further cause the processor to:
identify an interaction being performed by the user, wherein the signal characteristic is determined based on the interaction.

10. The system of claim 1, wherein:
receiving the set of neuromuscular signals comprises receiving the set of neuromuscular signals during a first session; and
determining the signal characteristic comprises prospectively determining the signal characteristic during a second session based on the set of neuromuscular signals received during the first session.

11. The system of claim 1, wherein dynamically reconfiguring the processing of neuromuscular signals comprises:
determining that a user will engage in an activity; and
adjusting the use of the neuromuscular sensors in a configuration customized to the activity.

12. The system of claim 1, wherein dynamically reconfiguring the processing of neuromuscular signals is based at least in part on a user profile of the user.

13. A computer-implemented method comprising:
receiving a set of neuromuscular signals from a plurality of neuromuscular sensors that detect a plurality of neuromuscular signals from a user;

determining, via a real-time system, at least one signal characteristic included in a first neuromuscular signal from the set of neuromuscular signals, wherein the first neuromuscular signal is associated with a first neuromuscular sensor included in the plurality of neuromuscular sensors; and dynamically reconfiguring the processing of neuromuscular signals from the plurality of neuromuscular sensors based on an output from at least one multiplexer in communication with the plurality of neuromuscular sensors.

14. The computer-implemented method of claim 13, wherein dynamically reconfiguring the processing of neuromuscular signals from the plurality of neuromuscular sensors comprises replacing use of the first neuromuscular sensor with use of a second neuromuscular sensor within the plurality of neuromuscular sensors.

15. The computer-implemented method of claim 13, wherein dynamically reconfiguring the processing of neuromuscular signals from the plurality of neuromuscular sensors comprises adjusting the amount of data being collected from the first neuromuscular sensor by upsampling or downsampling.

16. The computer-implemented method of claim 13, wherein determining the at least one signal characteristic comprises a signal propagation direction associated with the first neuromuscular signal.

17. The computer-implemented method of claim 13, wherein determining the at least one signal characteristic comprises detecting a loss of contact between the first neuromuscular sensor and the user's skin.

18. The computer-implemented method of claim 17, wherein detecting the loss of contact comprises at least one of:
determining that the neuromuscular signal comprises an amplitude outside a predetermined range; or
determining that the neuromuscular signal comprises a frequency discontinuity.

19. The computer-implemented method of claim 13, further comprising identifying an interaction being performed by the user, wherein the signal characteristic is determined based on the interaction.

20. A non-transitory computer-readable medium encoded with a plurality of instructions that, when executed by at least one computer processor, performs a method comprising:
receiving a set of neuromuscular signals from a plurality of neuromuscular sensors within an arrangement of neuromuscular sensors that detect a plurality of neuromuscular signals from a user;
determining, via a real-time system, at least one signal characteristic included in a first neuromuscular signal from the set of neuromuscular signals, wherein the first neuromuscular signal is associated with a first neuromuscular sensor included in the plurality of neuromuscular sensors; and
dynamically reconfiguring the processing of neuromuscular signals from the plurality of neuromuscular sensors based on an output from at least one multiplexer in communication with the plurality of neuromuscular sensors.

* * * * *